United States Patent
Geist

(10) Patent No.: US 7,246,622 B2
(45) Date of Patent: *Jul. 24, 2007

(54) CARBON DIOXIDE INDICATING APPARATUS, PARTICULARLY, DISK-LIKE CARBON DIOXIDE INDICATING APPARATUS

(75) Inventor: Leroy D. Geist, Parker, CO (US)

(73) Assignee: Vital Signs, Inc., Totowa, NJ (US)

( * ) Notice: Subject to any disclaimer, the term of this patent is extended or adjusted under 35 U.S.C. 154(b) by 447 days.

This patent is subject to a terminal disclaimer.

(21) Appl. No.: 10/926,559

(22) Filed: Aug. 26, 2004

(65) Prior Publication Data

US 2005/0016543 A1 Jan. 27, 2005

Related U.S. Application Data

(63) Continuation-in-part of application No. 10/266,294, filed on Oct. 8, 2002, now Pat. No. 6,929,008.

(51) Int. Cl.
*A62B 9/00* (2006.01)

(52) U.S. Cl. .......................... 128/205.23; 128/202.22; 128/202.27; 128/207.14

(58) Field of Classification Search ........... 128/207.14, 128/205.25, 202.22, 202.27, 207.17; 600/532, 600/353; 604/37, 75, 132, 133, 212, 516, 604/910, 911, 912
See application file for complete search history.

(56) References Cited

U.S. PATENT DOCUMENTS

| | | | | |
|---|---|---|---|---|
| 3,067,015 A | * | 12/1962 | Lawdermilt | 422/56 |
| 4,691,701 A | * | 9/1987 | Williams | 128/207.14 |
| 4,879,999 A | * | 11/1989 | Leiman et al. | 128/207.14 |
| 6,058,933 A | * | 5/2000 | Good et al. | 128/205.13 |
| 6,502,573 B1 | | 1/2003 | Ratner | 128/207.17 |
| 6,584,974 B1 | | 7/2003 | Ratner | 128/205.23 |

* cited by examiner

*Primary Examiner*—Michael J. Hayes
*Assistant Examiner*—Michael G. Mendoza
(74) *Attorney, Agent, or Firm*—R. Gale Rhodes, Jr.

(57) ABSTRACT

Carbon dioxide indicator for receiving gas containing carbon dioxide and for providing a visible indication of the presence of carbon dioxide in the gas, the indicator includes a connector for removably connecting the indicator to a source of gas containing carbon dioxide and which connector is for communicating at least a portion of such gas to the indicator. The carbon dioxide indicator may be a disk indicator and the connector may be a male luer or a locking male luer. The carbon dioxide indicator may include removable ultraviolet radiation shielding permitting the carbon dioxide indicator to be preassembled to a patient's respiratory or breathing circuits or to a resuscitator.

25 Claims, 26 Drawing Sheets

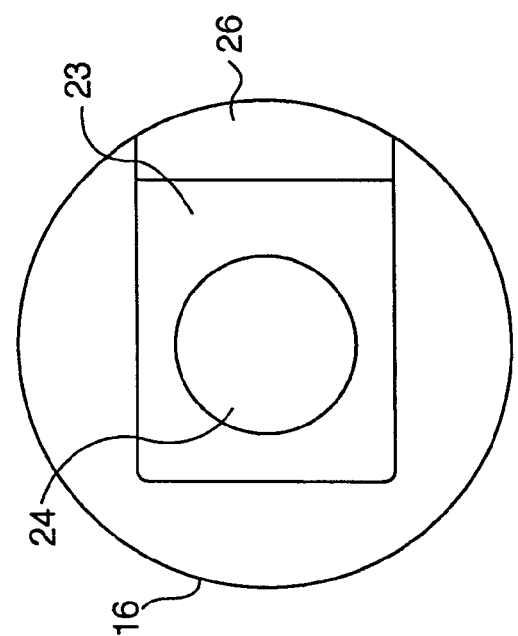
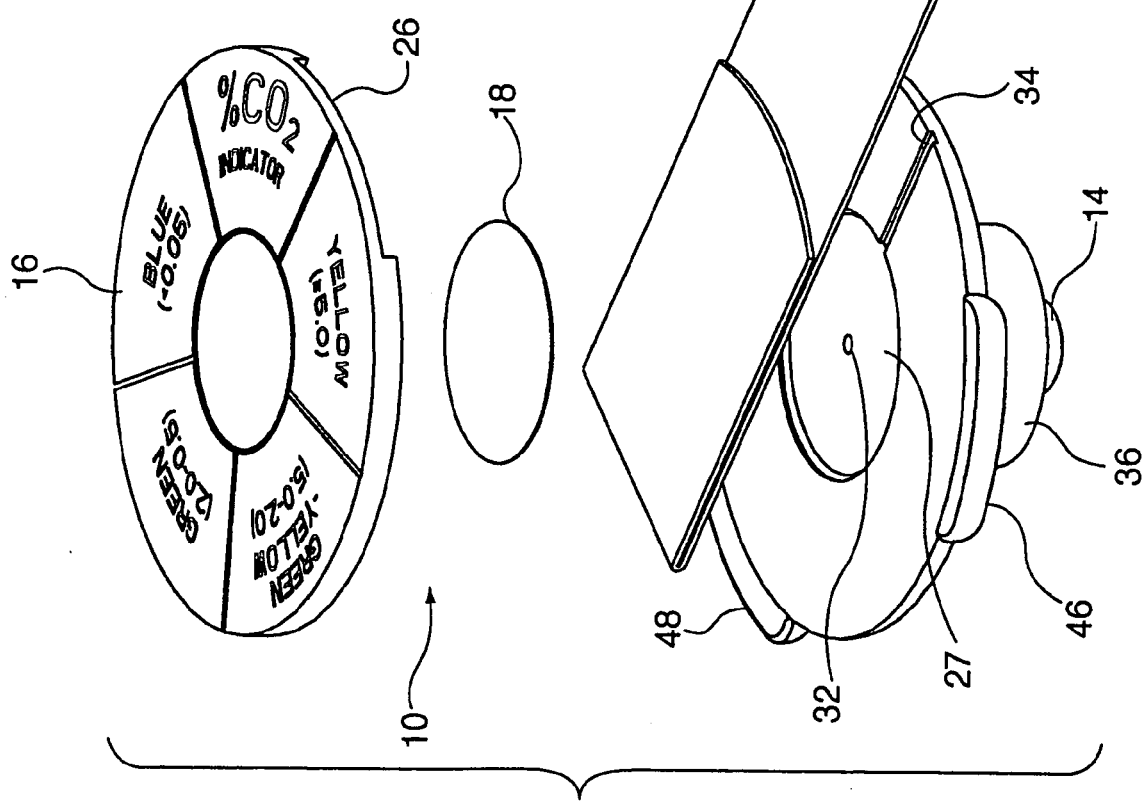

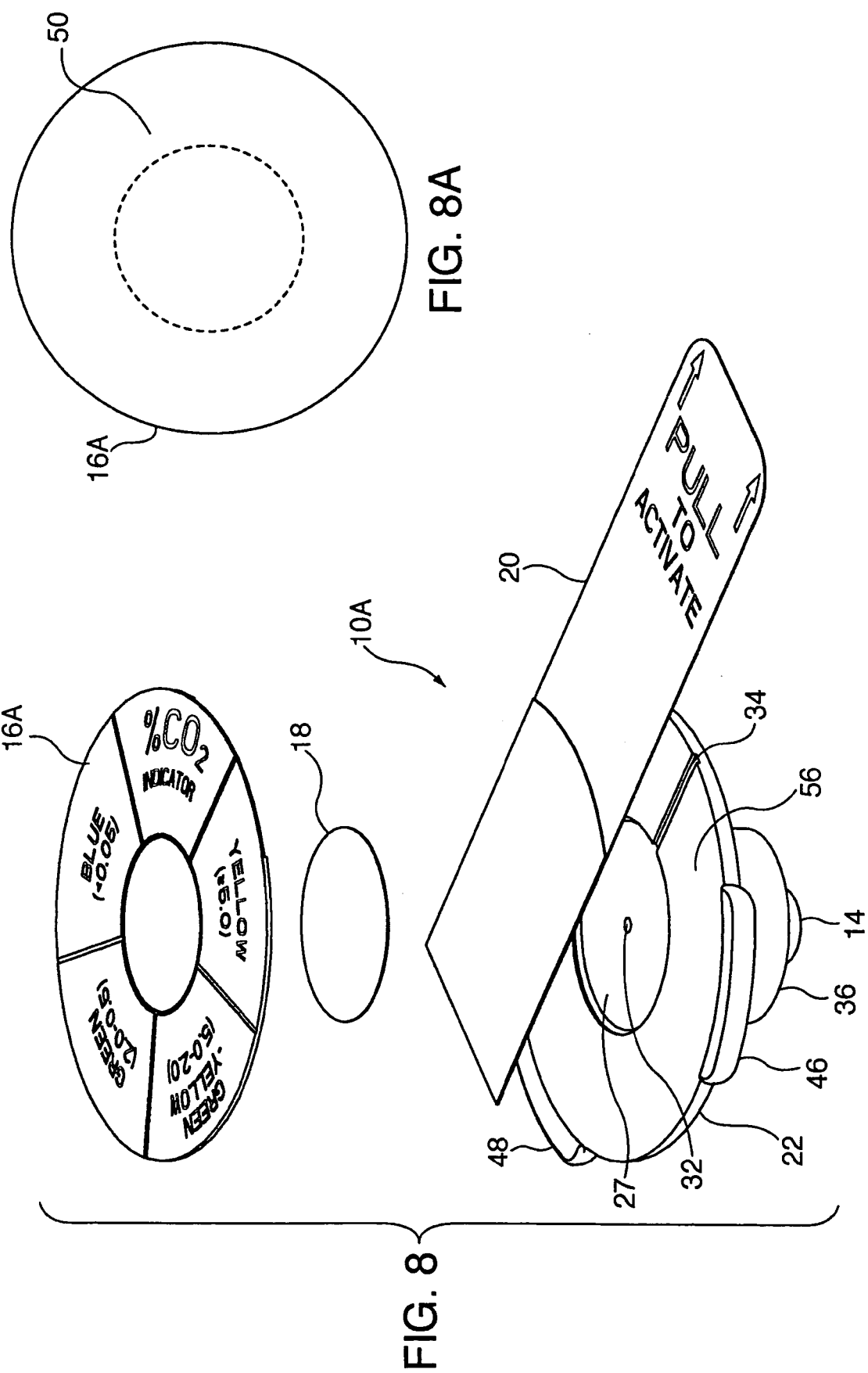

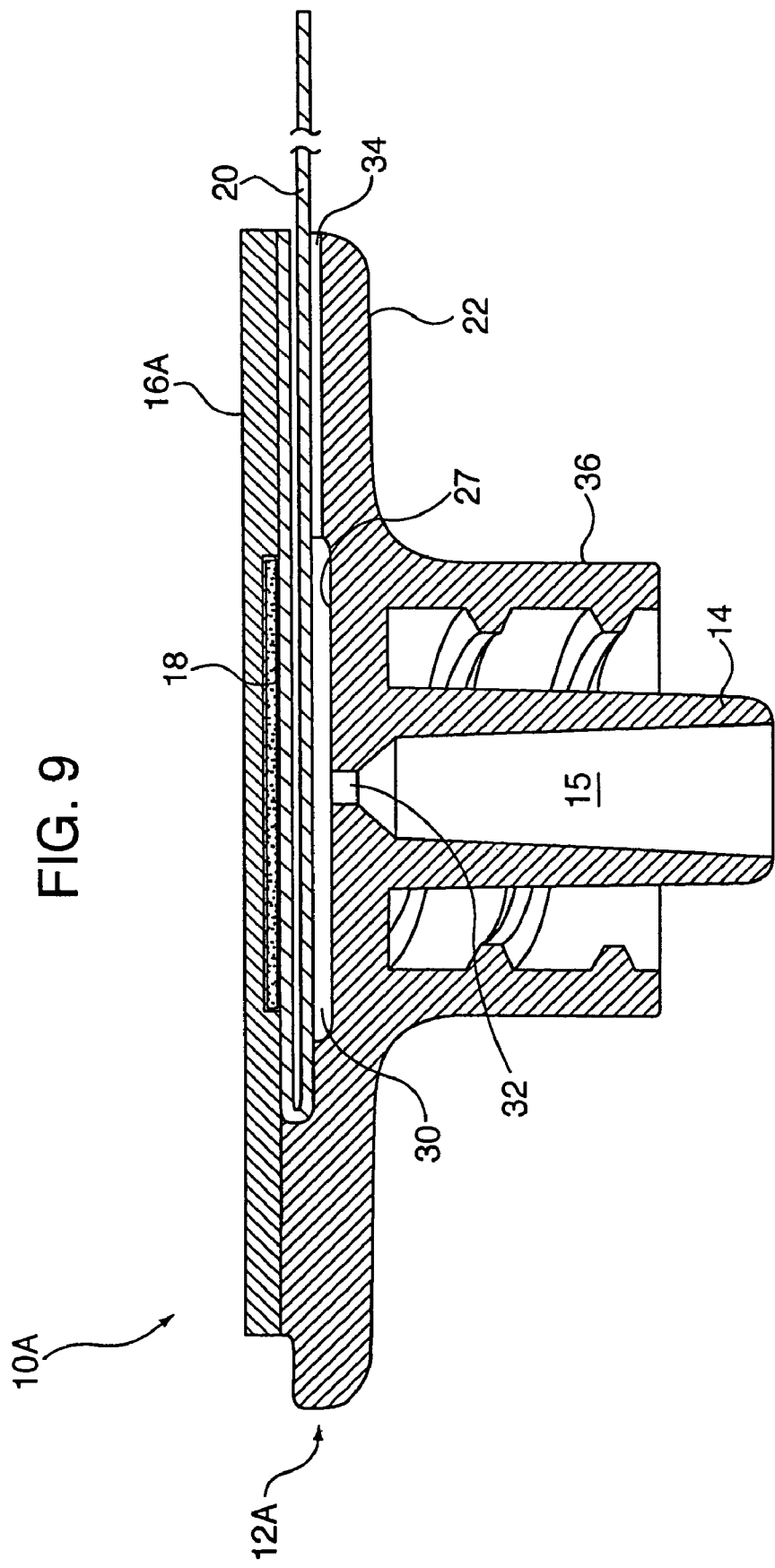

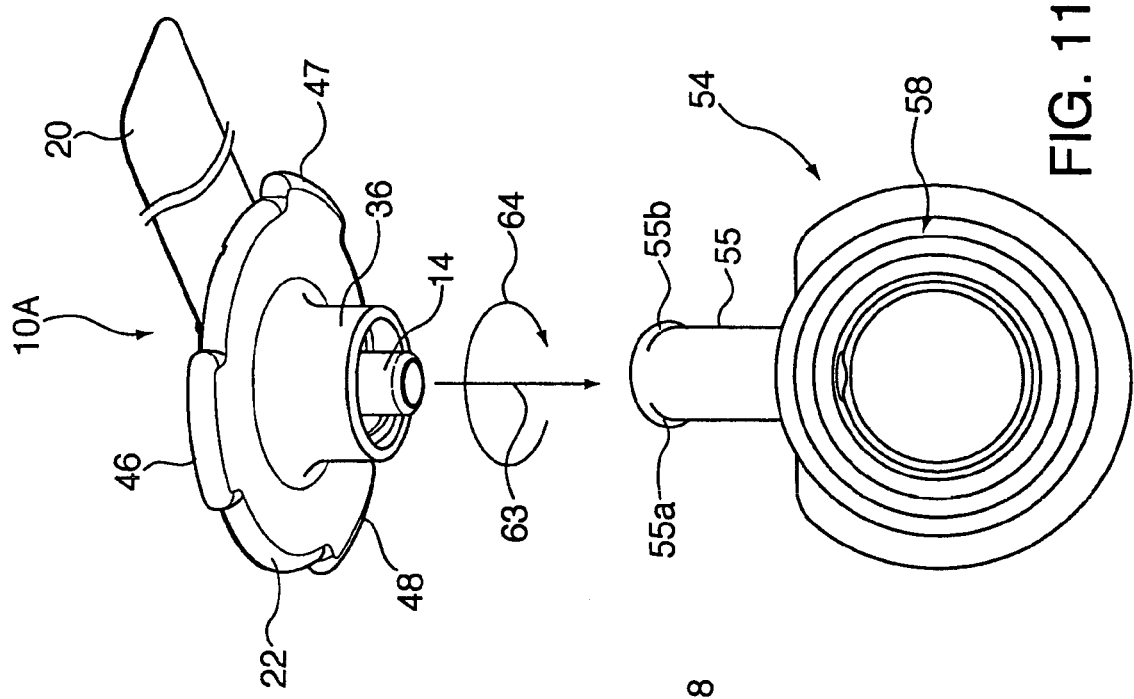
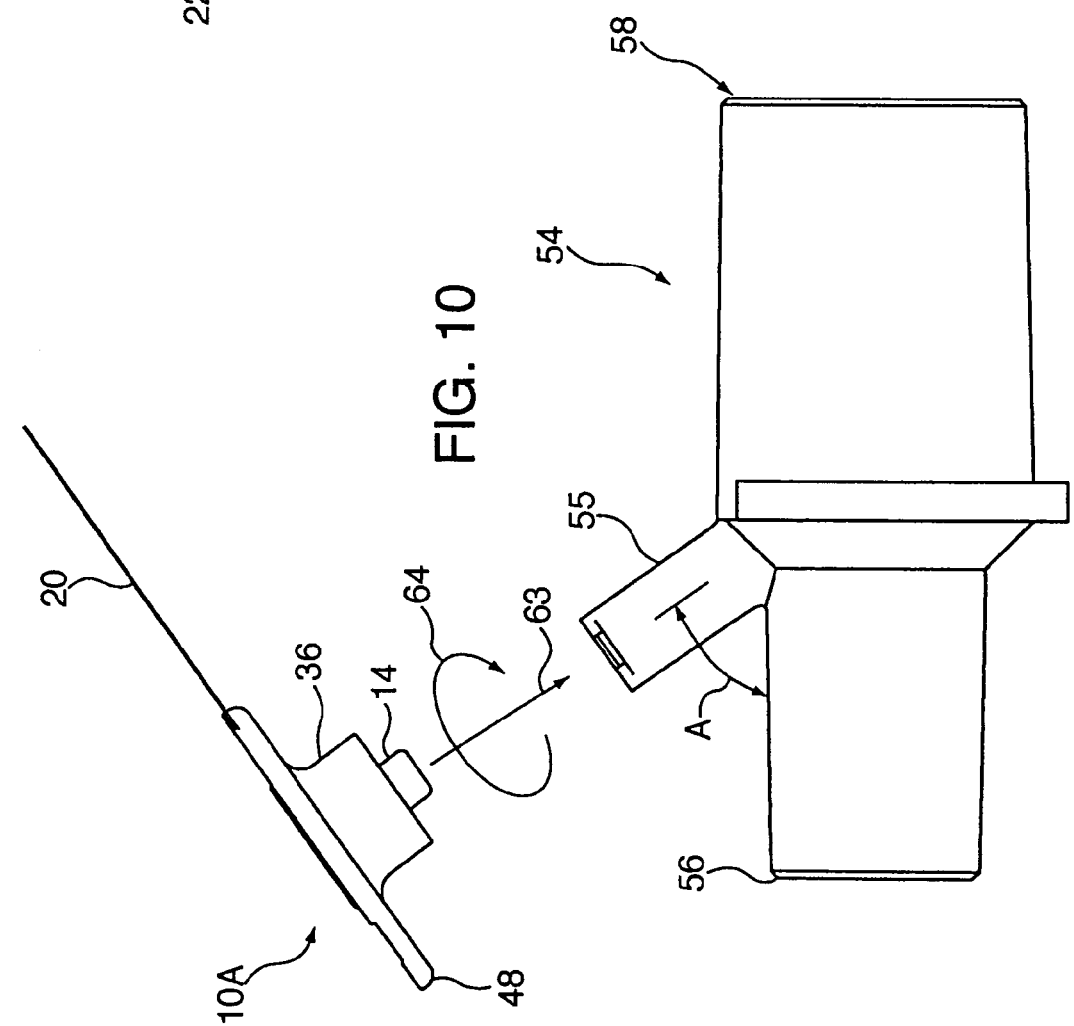

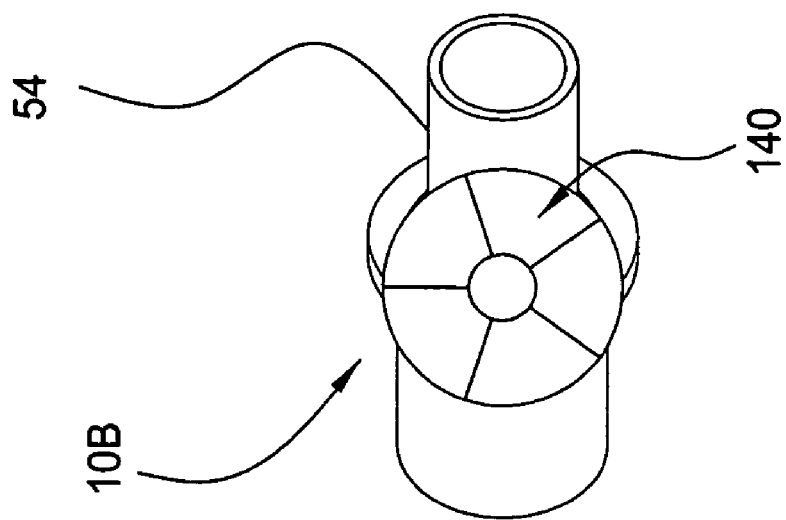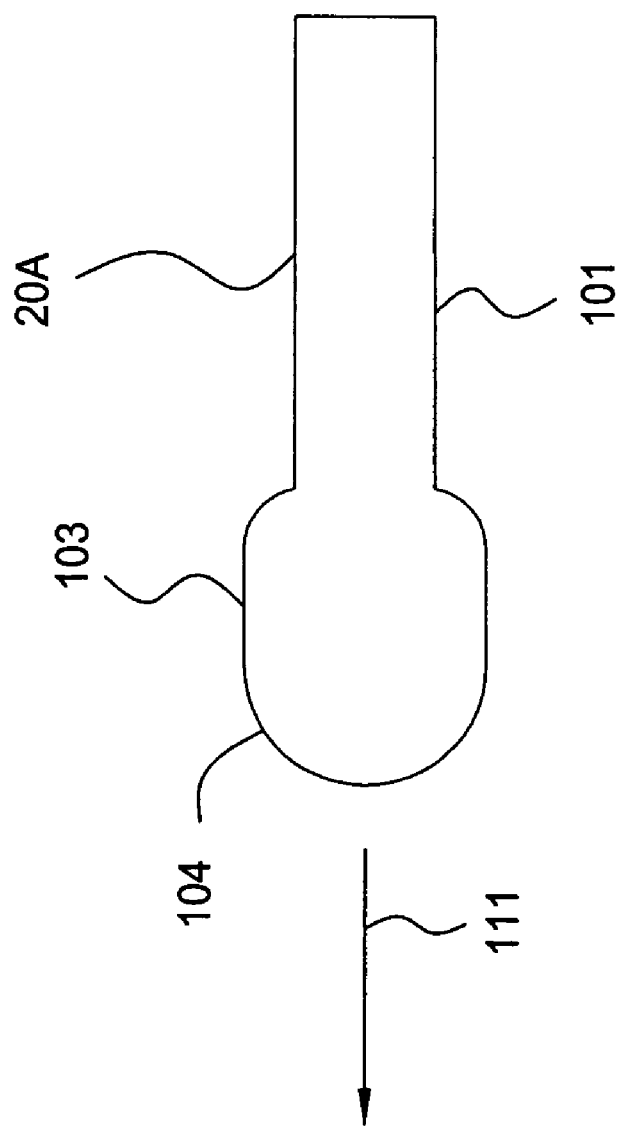
FIG. 24

CARBON DIOXIDE INDICATING APPARATUS, PARTICULARLY, DISK-LIKE CARBON DIOXIDE INDICATING APPARATUS

CROSS-REFERENCE TO RELATED APPLICATION

This application is a continuation-in-part application of application Ser. No. 10/266,294 filed Oct. 8, 2002, now U.S. Pat. No. 6,929,008 entitled CARBON DIOXIDE INDICATING APPARATUS, etc., Leroy D. Geist inventor and assigned to the same assignee as the present application.

BACKGROUND OF THE INVENTION

This invention relates generally to carbon dioxide indicating apparatus and more particularly relates to carbon dioxide indicating apparatus particularly useful with respiratory circuits, or breathing circuits, to determine whether the gas in such circuits contains carbon dioxide. Further, the carbon dioxide indicating apparatus of the present invention is particularly useful in determining concentrations of carbon dioxide in the above-noted gas. Still further particularly, the carbon dioxide indicating apparatus of the present invention is particularly useful in determining the correct placement of an intubation tube, or endotracheal tube, in the trachea of a patient.

Numerous carbon dioxide indicating apparatus are known to the art. For example, U.S. Pat. No. 5,005,572, patented Apr. 9, 1991, entitled $CO_2$ INDICATOR AND THE USE THEREOF TO EVALUATE THE PLACEMENT OF TRACHEAL TUBES, Raemer et al., inventors, discloses carbon dioxide indicating apparatus; this patent is hereby incorporated herein by reference as if fully reproduced herein. This incorporated patent discloses $CO_2$ indicators particularly useful for determining whether a tracheal tube is properly positioned within the trachea of a patient or improperly positioned in the patient's esophagus. This determination, as taught in detail in this incorporated patent, can be of lifesaving consequences. This determination, as also taught in detail in this incorporated patent, is based on the accepted reports that gas, such as a patient's exhalation gas, expelled from the patient's trachea contains from 4% to 6% $CO_2$ while gas expelled from the patient's esophagus contains no or extremely small amounts of $CO_2$. Accordingly, upon the $CO_2$ indicating device of this incorporated patent indicating the presence of carbon dioxide in such range, (4% to 6%) it is determined that the tracheal tube has been correctly positioned in the trachea of the patient and if such carbon dioxide concentration is not indicated, the determination is made that the tracheal tube has been incorrectly positioned in the patient's esophagus.

Other carbon dioxide indicating apparatus are known to the art such as, for example, the device shown in FIG. 1 of U.S. Pat. No. 4,879,999 patented Nov. 14, 1989, entitled DEVICE FOR THE DETERMINATION OF PROPER ENDOTRACHEAL TUBE PLACEMENT, Leiman et al. inventors. Upon the $CO_2$ indicator 12 of the embodiment shown in FIG. 1 of the patent failing, the entire endotracheal tube must be removed causing interruption of the patient anesthesia/ventilation procedure. Such endotracheal tube extubation and interruption of the patient's anesthesia/ventilation procedure is undesirable.

Carbon dioxide indicators are further useful in connection with other medical devices such as, for example, for being placed in the inspiratory path of a patient's anesthesia/ventilating circuit to determine if the carbon dioxide absorber is functioning properly and removing the desired carbon dioxide. This need is disclosed in lines 18-35 of column 1 of U.S. Pat. No. 2,890,177, patented Jun. 9, 1959, entitled CARBON DIOXIDE INDICATOR, Thoburn H. Kilmer inventor. This patent is hereby incorporated by reference as if fully reproduced herein.

A colorimetric carbon dioxide indicator known to the art and referred to as the Colibri calorimetric carbon dioxide indicator includes a male luer for connection to the female luer provided on the tubular member through which gas containing carbon dioxide, such as a patient's exhalation gas, flows. The Colibri calorimetric carbon dioxide indicator includes a trapezoidal carbon dioxide indicator provided with indicia indicative of various concentrations of carbon dioxide and which indicator turns different colors upon detecting different carbon dioxide concentrations. The Colibri carbon dioxide indicator is aligned axially with its male luer connector.

Accordingly, there is a need in the art for new and improved $CO_2$ detection or indicating apparatus and particularly new and improved carbon dioxide indicating apparatus that can be removed or replaced without interruption of the patient anesthesia/ventilation procedure.

As is further known to the art, some carbon dioxide indicating material is subject to degradation upon exposure to ultraviolet radiation and therefore must be shielded from ultraviolet radiation prior to use. Typically, the prior art carbon dioxide indicator containing such carbon dioxide indicating material is packaged separately in a package made of material which reflects and shields such carbon dioxide indicating material from ultraviolet radiation. Further typically such packaging is made of metal foil or is a package which contains a layer of metallized material. Such separate packaging, as is further known to the art, prevents such prior art carbon dioxide indicator from being pre-assembled to respiratory or breathing circuits and in particular prevents such prior art carbon dioxide indicator from being pre-assembled to a resuscitator for immediate use in a life saving situation. The time required to remove such prior art carbon dioxide indicator from such packaging and then mount it to the resuscitator can cause the loss of valuable time which needs to be spent in the life saving procedure.

Accordingly, there is a need in the art for carbon dioxide indicating apparatus which is provided with ultraviolet radiation shielding and which can be pre-assembled to a patient's respiratory or breathing circuits, particularly to the above-noted resuscitator, and which carbon dioxide indicating apparatus permits the ultraviolet shielding to be readily, virtually instantaneously, removed enabling immediate use of such resuscitator.

SUMMARY OF THE INVENTION

Carbon dioxide indicating apparatus embodying the present invention may include a disk-like carbon dioxide indicator for receiving gas containing carbon dioxide and for providing a visual indication of the presence of carbon dioxide in the gas. Such indicator may include a connector for removably connecting the indicator to a source of gas containing carbon dioxide and which connector is for communicating at least a portion of such gas to the indicator. Such carbon dioxide indicating apparatus may include ultraviolet radiation shielding which may be readily removed enabling preassembly of the apparatus to various respiratory or breathing circuits and by way of specific example to the above-noted resuscitator.

DESCRIPTION OF THE DRAWINGS

FIG. 2 is an exploded view of the apparatus of FIG. 1;

FIG. 2A is a bottom view of the cover disk shown in FIG. 2;

FIG. 8 is an exploded view of the embodiment of FIG. 7;

FIG. 8A is a bottom view of the cover disk shown in FIG. 8;

FIG. 9 is a cross-sectional view taken generally along the line 9-9 in FIG. 7 in the direction of the arrows;

FIGS. 10 and 11 are, respectively, side and end views of a third embodiment of carbon dioxide indicating apparatus of the present invention;

FIG. 24 is a diagrammatical illustration of the removal of the elongated foldable blocking member;

DETAILED DESCRIPTION OF THE INVENTION

Figure 3:
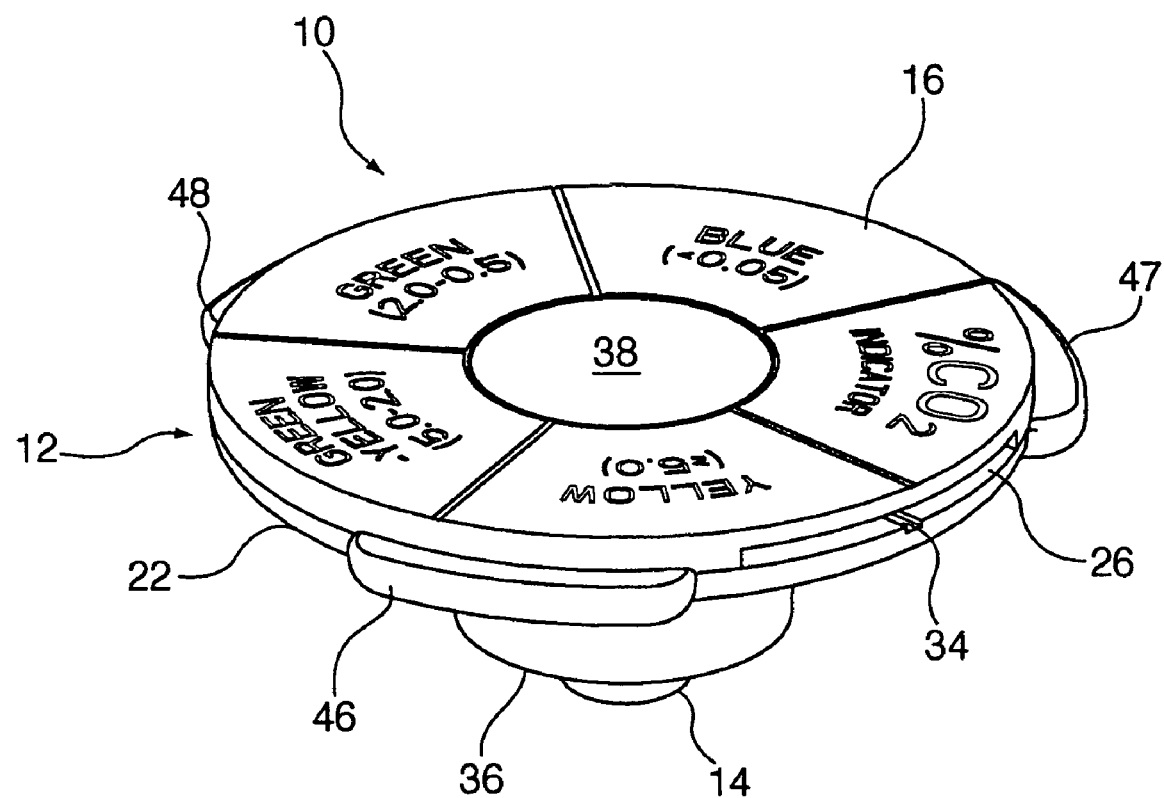
FIG. 3 is a perspective view of the embodiment of FIG. 1 with the activation pull tab removed.
Figure 4:
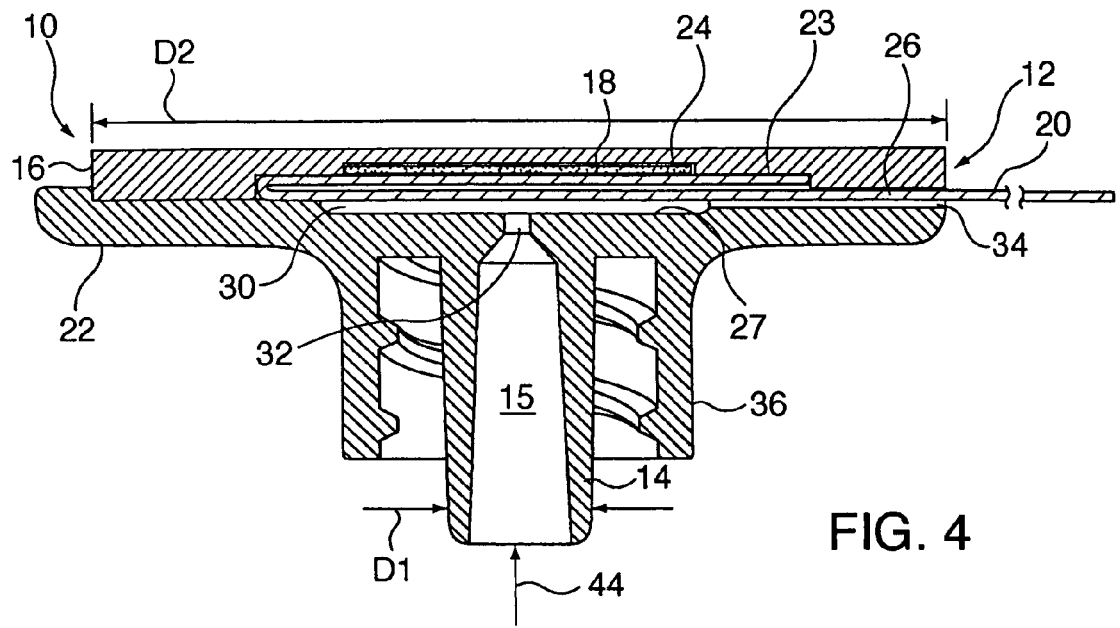
FIG. 4 is a cross-sectional view taken generally along the line 4-4 in FIG. 1 in the direction of the arrows.
Figure 5:
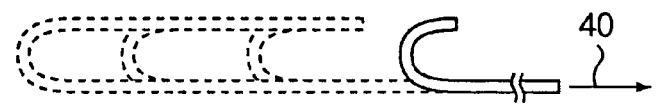
FIG. 5 is a diagrammatical illustration of the successive stages of the unfolding and removal of the activation pull tab.
Figure 6:
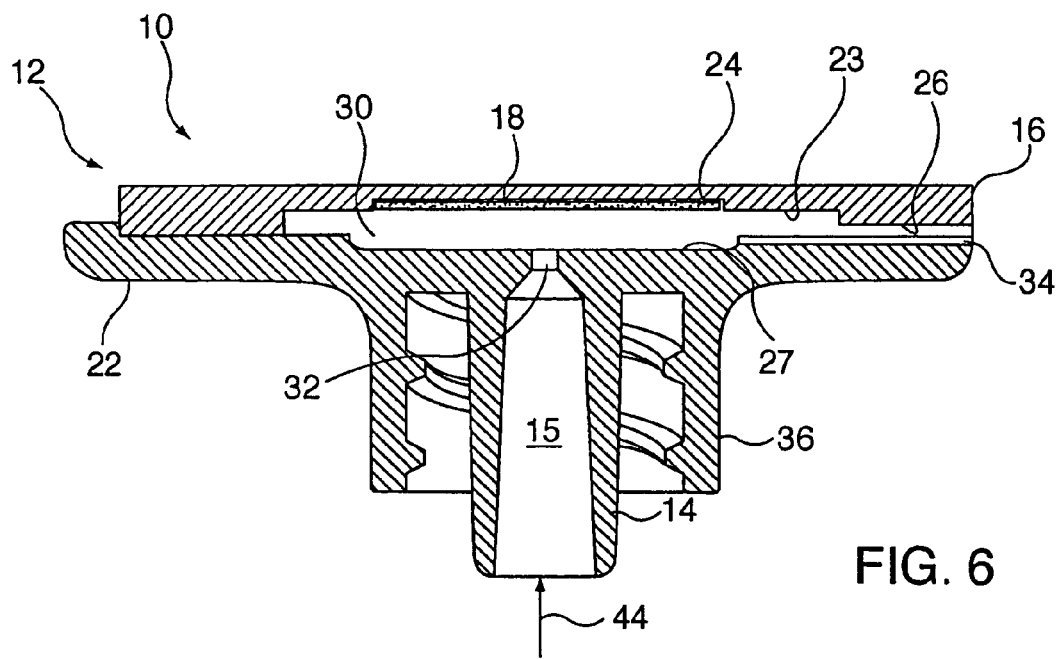
FIG. 6 is a cross-sectional view similar to FIG. 4 but with the activation pull tab removed.

Referring to FIGS. 1-6, carbon dioxide indicating apparatus indicated by general numerical designation 10 and embodying the present invention includes a generally circular disk-like portion or member indicated by general numerical designation 12, a tubular member 14, a body of visual indicating material 18 and an activation pull tab 20. The disk-like portion 12, note particularly FIGS. 4 and 6, provides a central internal chamber 30 for receiving the visual indicating material 18 and the leftward folded end portion of an activation tab 20. The disk-like portion 12 provides a radial slot 34 extending between the chamber 30 and the atmosphere and for placing the chamber and the indicating material 18 in fluid communication with the atmosphere upon the activation pull tab 20 being removed as shown in FIG. 6. The tubular member 14, best seen in cross-section in FIGS. 4 and 6, provides an internal passageway 15 in fluid communication with the chamber 30 and, upon the activation pull tab 20 being removed as shown in FIG. 6, the central chamber 30 and the visual indicating material 18 are placed in fluid communication with the tubular member passageway 15. Gas, indicated by the upwardly extending arrow 44 in FIGS. 4 and 6, containing carbon dioxide, from a source, such as a patient's exhaled breath, enters the tubular member passageway 15, FIG. 6, flows into the chamber 30 and engages and interacts or reacts with the body of visual indicating material 18 to cause the body to provide a visual indication of the presence of the carbon dioxide, such as by changing color, after which the gas exits to the atmosphere through the radial slot 34. The visual change provided by the body of material 18, such as the noted color change, is visible to an external observer through the top of the disk-like member 12 due to at least the upper central portion thereof being sufficiently transparent to permit the visual indication, e.g., color change, provided by the indicating material 18 to be seen therethrough. It will be noted from FIGS. 4 and 6 that the passageway 15 and the radial slot 34 are disposed substantially perpendicularly to each other, are disposed by substantially 90° with respect to each other, which permits a person viewing the carbon dioxide color indicating change not to have the patient's exhaled breath exiting the radial slot 34 blow into the observer's face.

Further generally, from FIG. 4, it will be understood that the tubular member 14 has an outer diameter D1 and the disk-like member 12 has an outer diameter D1 larger than the outer diameter D2, and it will be further noted from FIG. 4 that the disk-like portion 12 is provided or disposed transversely, perpendicularly as shown, at the upper end of the tubular member 14.

More particularly, and referring to the exploded view of FIG. 2, it will be understood that the carbon dioxide indicating apparatus 10 includes a generally circular cover disk 16, the above-noted activation pull tab 20 and a generally circular base disk 22. The bottom portion of the cover disk 16 (note FIGS. 2A, 4 and 6), is provided with an inwardly extending and centrally formed rectangular recess 23 and an inwardly extending and centrally formed circular recess 24 extending inwardly from the rectangular recess 23, and a radially disposed generally rectangular slot 26. The rectangular recess 23 and the rectangular slot 26 are complementary in shape to the transverse cross-section of the activation pull tab 20 and slidably receive the leftward or inner end portion of the pull tab 20; the slot 26, particularly its entrance, is best seen in FIG. 2. The base disk 22 is provided with an inwardly extending and centrally formed circular recess 27, note FIGS. 2, 4 and 6, the above-noted radial slot 34 and, upon the components comprising the carbon dioxide indicating apparatus 10 being assembled as shown in FIG. 4, the recesses formed in the cover disk 16 and the recess formed in the base disk 22 cooperatively provide the generally central internal chamber or cavity 30 noted above; it will be further noted that upon such assembly the slot 26 formed in the cover disk 16 partially overlies the slot 34 formed in the base disk, note particularly FIGS. 4 and 6.

Figure 1:
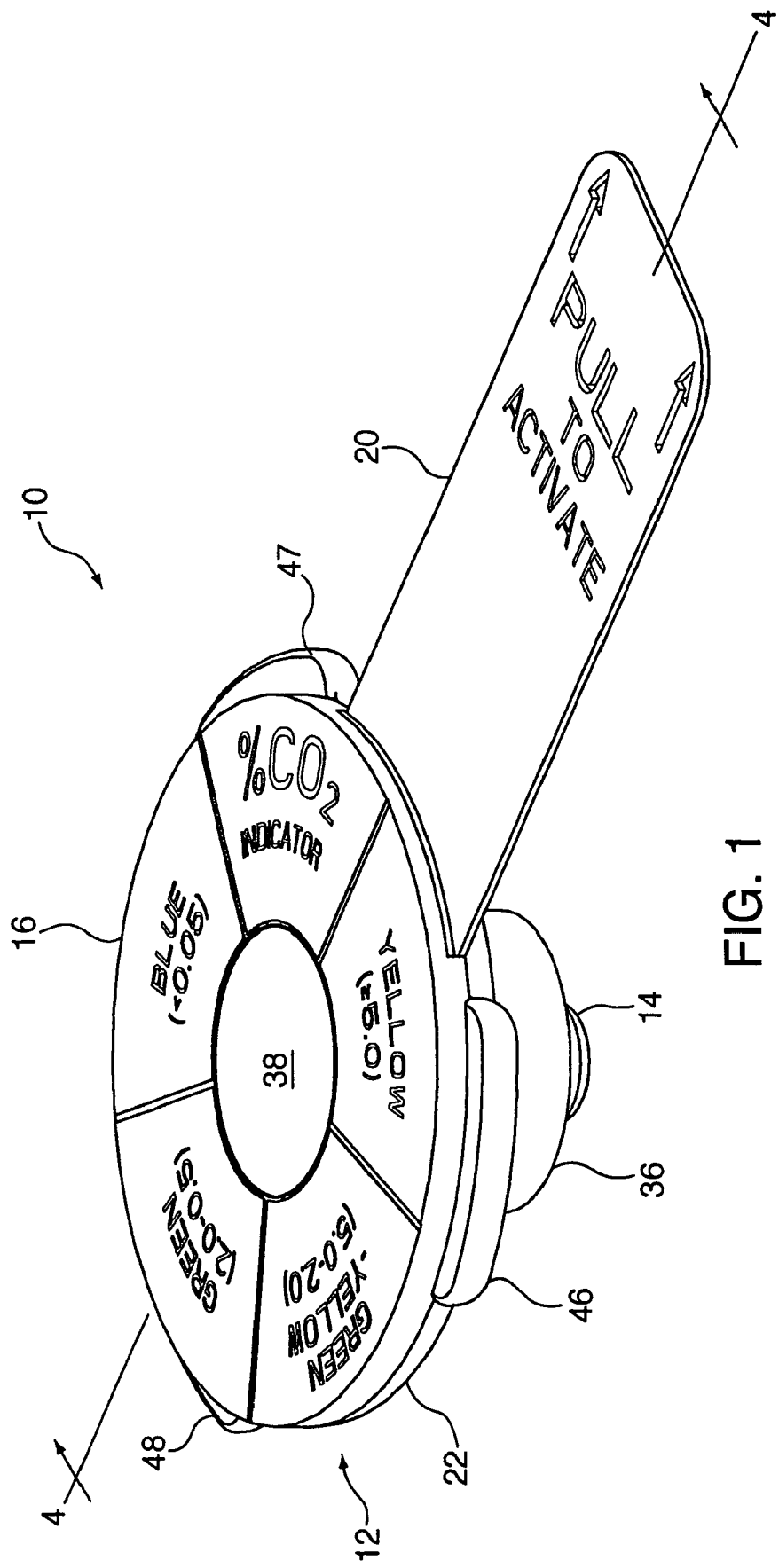
FIG. 1 is a perspective view of a first embodiment of carbon dioxide indicating apparatus embodying the present invention.

As will be understood from FIG. 4, the leftward or inner end portion of the activation pull tab 20 is folded back upon itself with the free end thereof residing on top. Upon assembly, and referring further to FIG. 4, the circular disk 18 of visual indicating material resides in the circular recess 24 provided in the cover disk 16 and on top of the folded leftward end portion of the activation pull tab 20 which resides in the rectangular recess 23 provided in the cover disk 16. Further upon such assembly, and referring further to FIG. 4, the rightward end or end portion of the activation pull tab 20 resides in and extends radially outwardly through the slot 26 formed in the cover disk 16 (FIGS. 2A and 4) and extends radially outwardly from the apparatus 10 as shown in FIGS. 1 and 4.

Figure 4A:
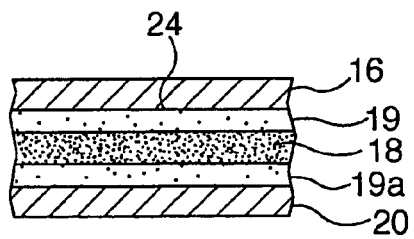
FIG. 4A is a diagrammatical cross-sectional illustration of an embodiment of mounting or positionment of a layer of visual indicating material.

More particularly with regard to the mounting or positionment of the circular disk 18 of visual indicating material, FIG. 4A, during and in final assembly, a suitable layer of substantially transparent adhesive 19 may be provided intermediate the portion of the cover disk 16 providing the circular recess 24 and the visual indicating material 18 and an annular layer of suitable adhesive 19a may be provided intermediate the visual indicating material 18 and the folded top of the activation pull tab 20; the layer of adhesive 19a is annular to prevent the center portion of the underside of the circular disk 18 of visual indicating material 18 being coated with the adhesive and thereby reducing, or impairing, its effectiveness and ability of the material 18 to react with carbon dioxide upon exposure thereto and provide the visual indication.

Referring again to FIGS. 2, 4 and 6, it will be understood that the base disk 22 is provided with a centrally formed cylindrical opening 32 for placing the internal chamber 30 and disk 18 of visual indicating material in fluid communication with the passageway 15 formed in the tubular member 14 upon the activation pull tab 20 being removed as shown in FIG. 6 and as described in detail below. Referring further to FIG. 2, it will be noted that the inner or leftward folded end portion of the activation pull tab 20 is larger in length and width than the diameter of the circular disk 18 of visual indicating material. Accordingly, due to these relative dimensions, it will be understood that upon the components of the carbon dioxide indicating apparatus 10 being assembled as shown in FIG. 4, that the folded leftward end portion of the activation pull tab 20 acts as a seal, or blocking member, sealing or blocking off the disk 18 of visual indicating material from fluid communication with the passageway 15 formed in the tubular member 14, thereby sealing or blocking off the disk 18 of visual indicating material from the carbon dioxide containing gas 44, and sealing or blocking off the disk 18 of visual indicating material from the atmosphere by blocking or sealing off the radial slot 34 formed in the base disk 22; it will be understood that in the context of the present invention such sealing or blocking of the disk 18 of visual indicating material is the deactivation of such material. It will be understood that the cylindrical opening 32 will be suitably sized so as to appropriately and acceptably determine the leak rate of gas to the chamber 30 and through the chamber to the atmosphere upon the carbon dioxide containing gas 44 (FIG. 6) flowing through the carbon dioxide indicating apparatus 10.

It will be further understood from FIGS. 4 and 6 that the tubular member 14 may be a male luer of a type known to the art and from these FIGS. It will be further understood that the base disk 22 may be provided with an internally threaded collar 36 surrounding and spaced from the male luer 14 thereby providing in combination with the male luer 14 a locking male luer. Still further from FIGS. 4 and 6, it will be understood that the base disk 22, male luer 14 and collar 36 may be formed integrally.

With specific regard to the disk 18 of visual indicating material, it will be understood that in the preferred embodiment such material is calorimetric carbon dioxide indicating material available from BreGas AB, Ulvsundaragen, 178 B Se-166 67, Bromma, Sweden and sold under the calorimetric carbon dioxide indicating material identification C-it#05-76-1200-0. Generally, such calorimetric carbon dioxide indicating material will change color, by adsorption, and into a plurality of different colors, upon being exposed to gas containing different concentrations of carbon dioxide. For example, upon the disk 18 being such calorimetric carbon dioxide indicating material the disk will be blue in its normal state when not exposed to carbon dioxide and will remain blue upon being exposed to gas containing carbon dioxide having a concentration of less than 0.05%, will turn green upon being exposed to gas containing carbon dioxide having a concentration between 0.5% and 2%, will turn green yellow upon being exposed to gas having a carbon dioxide concentration from 2% to 5% and will turn yellow upon being exposed to gas having a carbon dioxide concentration at or above 5%.

As will be noted from FIGS. 1, 2 and 3, the top surface of the cover disk 12 may be provided with a plurality of radially disposed segments having the names of the colors blue, green, green-yellow and yellow imprinted or otherwise provided thereon and which colors, it will be noted, correspond to the foregoing noted colors into which the disk 18 turns upon being exposed to gas containing the above-noted concentrations of carbon dioxide. It will be further understood that at least the central portion 38 of the cover disk 16, surrounded by the radial segments, is sufficiently transparent to permit the disk 18 of colorimetric carbon dioxide indicating material to be seen therethrough by the eye of an observer, e.g., doctor, nurse, or clinician, who can compare the color into which the colorimetric carbon dioxide indicating material 18 changes with the corresponding color name provided on the top surface of the cover disk 22 and thereby know the concentration of carbon dioxide in the gas to which the disk 18 is exposed. Alternative to having the names of the colors imprinted on the top surface of the cover disk 16, the radial segments could themselves be colored blue, green, green-yellow and yellow. It will be understood that it is within the contemplation of the present invention that instead of such above-noted color changes being observed externally by the eye of an observer that such color changes may be scanned by suitable color optical scanning equipment known to the art with the scanned color information being usable to make various determinations in association with the determined concentrations of carbon dioxide in the observed gas.

Alternatively, the disk of carbon dioxide indicating material 18 may be the calorimetric carbon dioxide indicating material disclosed in EXAMPLE 2 at column 8, line 1 et seq. of U.S. Pat. No. 4,728,499, entitled CARBON DIOXIDE INDICATOR DEVICE patented Mar. 1, 1988, Fehder inventor, which patent is incorporated herein by reference. As taught in this EXAMPLE, such calorimetric carbon dioxide indicating material is blue upon being exposed to no carbon dioxide, turns green upon being exposed to 0.3% carbon dioxide and turns yellow upon being exposed to gas having a carbon dioxide concentration of 2%-5%.

The removal of the seal, blocking member or activation pull tab 20 is illustrated diagrammatically in FIG. 5. As shown in FIG. 4, and described above, initially the leftward end portion of the tab 20 occupies the folded position shown diagrammatically in FIG. 5 and, to activate the colorimetric carbon dioxide indicating material 18, the rightward end, or end portion, of the tab 20 is pulled rightwardly in the direction of the arrow 40 in FIG. 5 causing the leftward end portion of the tab 20 to unfold, or unroll, as indicated by the dashed lines in FIG. 5. The pull tab 20 is pulled sufficiently rightwardly, through the slot 26, FIGS. 3 and 4, until the tab 20 is entirely removed from the carbon dioxide indicating apparatus 10. Upon such removal, as noted above and as shown in detail in FIG. 6, the colorimetric carbon dioxide indicating material or disk 18 is placed in fluid communication with the passageway 15 formed in the tubular member or male luer 14 and in fluid communication with the atmosphere through the slot 34 formed in the base disk 22; in the context of the present invention such fluid communication of the disk 18 of visual indicating material is the activation of such material. Upon the carbon dioxide indicating material being mounted, or laminated, as described above and illustrated in FIG. 4A, and upon the activation pull tab 20 being unfolded or unrolled as described above, it will be understood that as the folded leftward end portion of such tab is unrolled or unfolded, the folded over portion of such tab will be peeled away from the carbon dioxide indicating material and break the adhesive bond provided between the activation pull tab 20 and the carbon dioxide indicating material 18 by the adhesive 19a.

In one embodiment of the carbon dioxide indicating apparatus 10 of FIGS. 1-6, the cover disk 16 was suitably molded such as, for example, by injection molding from a suitable, at least substantially transparent, thermoplastic material such as polycarbonate, the base disk 22 was suitably molded such as by injection molding from a suitable rigid thermoplastic material such as polycarbonate and the activation pull tab 20 was suitably formed, such as by die cutting, from, for example, silicone coated super calendared kraft paper. After assembly as shown in FIG. 4, the cover disk 18 and base dish 22 may be suitably connected together, or the cover disk 16 mounted to the base disk 22, such as by thermosonic welding or by solvent bonding. The disk 18 of visual indicating material, for example upon being one of the above-noted colorimetric carbon dioxide indicating materials, may be produced, such as for example by compacting or as described at column 3, lines 4-16 of incorporated U.S. Pat. No. 4,728,499.

In general operation, it will be assumed that the carbon dioxide indicating apparatus 10 of the present invention, FIG. 4, has been placed in fluid communication with a source of gas containing carbon dioxide as indicated by the upwardly extending arrow 44. Such fluid communication may be accomplished by rotating the apparatus 10 to cause the male locking luer comprised of the male luer 14 and surrounding internally threaded collar 36 to rotatably engage a female locking luer, not shown, but assumed to be extending outwardly from the source of gas containing carbon dioxide 44. Rotation of such male locking luer into engagement with such female locking luer causes, as known to the art, the male luer 14 of FIG. 4 to telescopically, slidably and wedgedly engage, in a fluid-tight fit, the associated female luer provided on such female locking luer. To facilitate rotation of the carbon dioxide indicating apparatus 10 of the present invention, as shown in FIGS. 1, 2 and 3, the base disk 22 may be provided with a plurality of radially disposed and outwardly extending tabs 46, 47 and 48. The activation pull tab 20 is removed, as indicated diagrammatically in FIG. 5 and described above, to activate the disk of visual indicating material 18, whereupon, as will be understood from FIG. 6, and as described generally above, the gas containing carbon dioxide indicated by the upwardly extending arrow 44 in FIGS. 4 and 6, will flow upwardly through the passage 15 formed by the male luer 14, into the chamber 30 and into engagement with the disk 18 of calorimetric carbon dioxide indicating material, to expose such material to the carbon dioxide contained in the gas, and such gas will flow outwardly of the apparatus 10 to the atmosphere through the slots 34 formed in the base disk 22. As noted above, depending upon the concentration of the carbon dioxide in such gas, the calorimetric carbon dioxide indicating material 18 upon reacting with the carbon dioxide, will turn, for example, yellow, green or blue providing such visible color indication thereof which will be viewed by such observer through the transparent central portion 38 of the cover disk 16 whereby an observer, as also noted hereinabove, can make a visual comparison of the color into which the indicating material 18 has turned with the corresponding name of the color provided on the top surface of the cover disk 22, thereby determining the carbon dioxide concentration of the gas introduced into the apparatus 10. It will be further understood that the apparatus 10 of the present invention may operate on a breath-to-breath basis as disclosed in the above incorporated 5,005,572 patent and provide one visible color upon the patient inhaling and a second visible color upon the patient exhaling.

Figure 7:
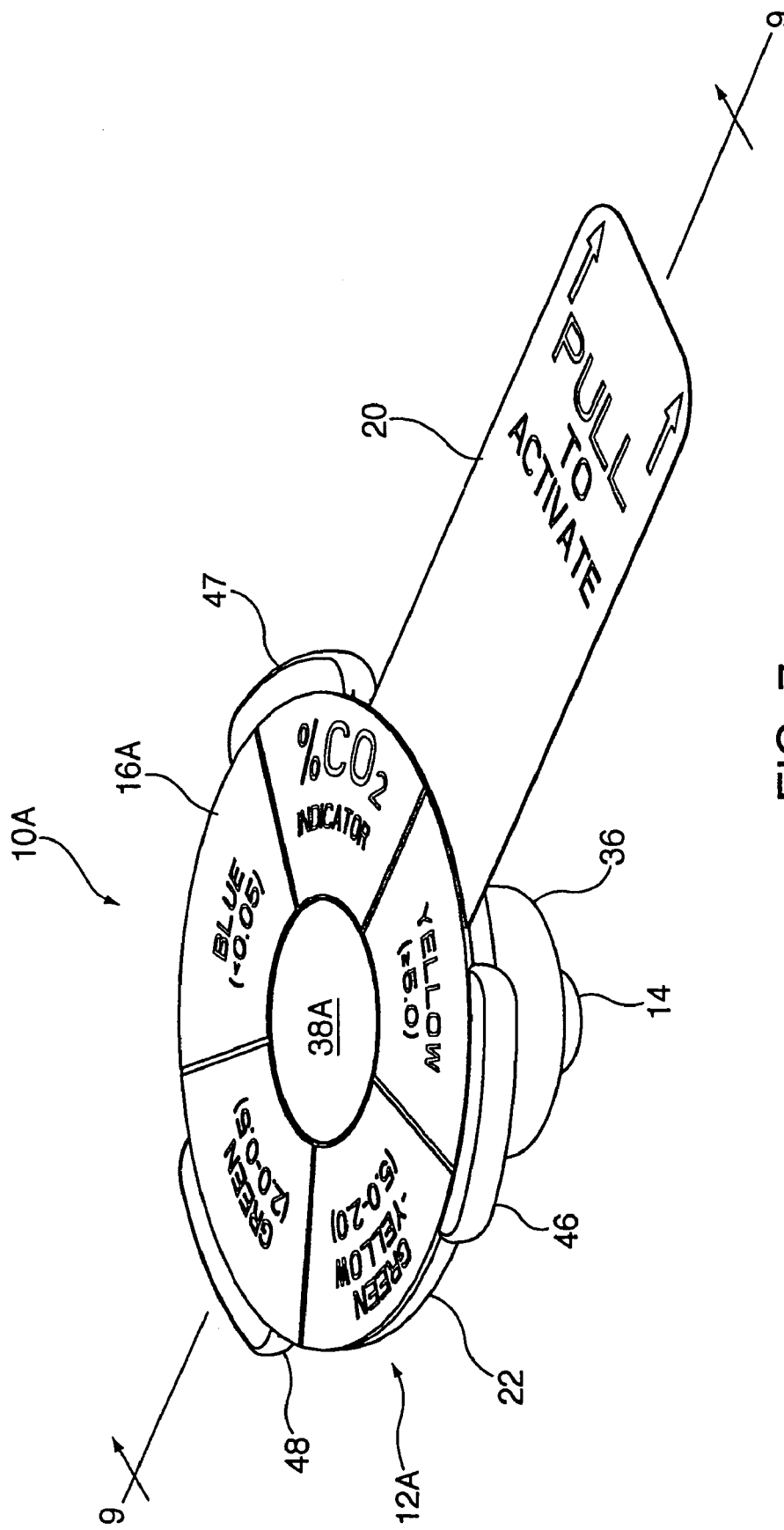
FIG. 7 is a perspective view of a second embodiment of carbon dioxide indicating apparatus embodying the present invention.

Referring now to FIGS. 7-9, an alternate embodiment of carbon dioxide indicating apparatus embodying the present invention is shown and indicated by general numerical designation 10A. Carbon dioxide indicating apparatus 10A is substantially the same as carbon dioxide indicating apparatus 10 described above and shown primarily in FIGS. 1-6. Accordingly, it will be understood that components or elements comprising apparatus 10A which are the same as the components in apparatus 10 are given the same numerical designations and will be understood to perform the same functions. The difference between apparatus 10A and apparatus 10 is that the cover disk 16a of apparatus 10A, FIGS. 7-9, is in the nature of a decal and is a disk of thin film, or thin plastic film, and may be, for example, a thin film disk of polycarbonate having a thickness of about 0.010". The thin film cover disk 16a may be transparent, or at least substantially transparent, and at least the central portion 38a is transparent, or at least substantially transparent, to permit the carbon dioxide indicating material 18 to be seen therethrough upon such material being calorimetric carbon dioxide indicating material and changing color in the presence of carbon dioxide as described above. The outer peripheral portion of the upper surface of the cover disk 16a is provided with the same indicia as the upper surface of the cover disk 16 of the earlier embodiment. Such indicia may be provided on the upper surface of the cover disk 16a such as, for example, by suitable printing or screen printing.

Referring to FIGS. 8 and 8A, and particularly to the bottom view of FIG. 8A, it will be understood that the outer peripheral portion of the bottom surface is provided with a layer of suitable adhesive, such as a coating or layer of suitable pressure sensitive adhesive, for adhering and thereby mounting the cover disk 16a to the outer peripheral portion 52 (FIG. 8) of the top surface of the base disk 22. It will be understood, from FIG. 9, that a portion of the adhesive on the under surface of the cover disk 16a adheres to the top layer of the folded back left end portion of the activation pull tab 20 and upon the pull tab being unrolled or unfolded as described above, and as indicated in FIG. 5, the pull tab peels away from the cover disk 6a. Further, it will be understood, that the carbon dioxide indicating material 18 of FIG. 8 may be mounted or positioned in place in the same manner as indicated in FIG. 4A and described above.

Referring now further generally to additional embodiments of the present invention illustrated in FIGS. 10-8, it will be understood that such further embodiments are illustrated, and will be described, in combination with the carbon dioxide indicating apparatus 10A of FIGS. 7-9, however, it will be understood that the carbon dioxide indicating apparatus embodiment 10 shown in FIGS. 1-6 is equally applicable to such combination and that such is contemplated by the present invention.

Figure 12:
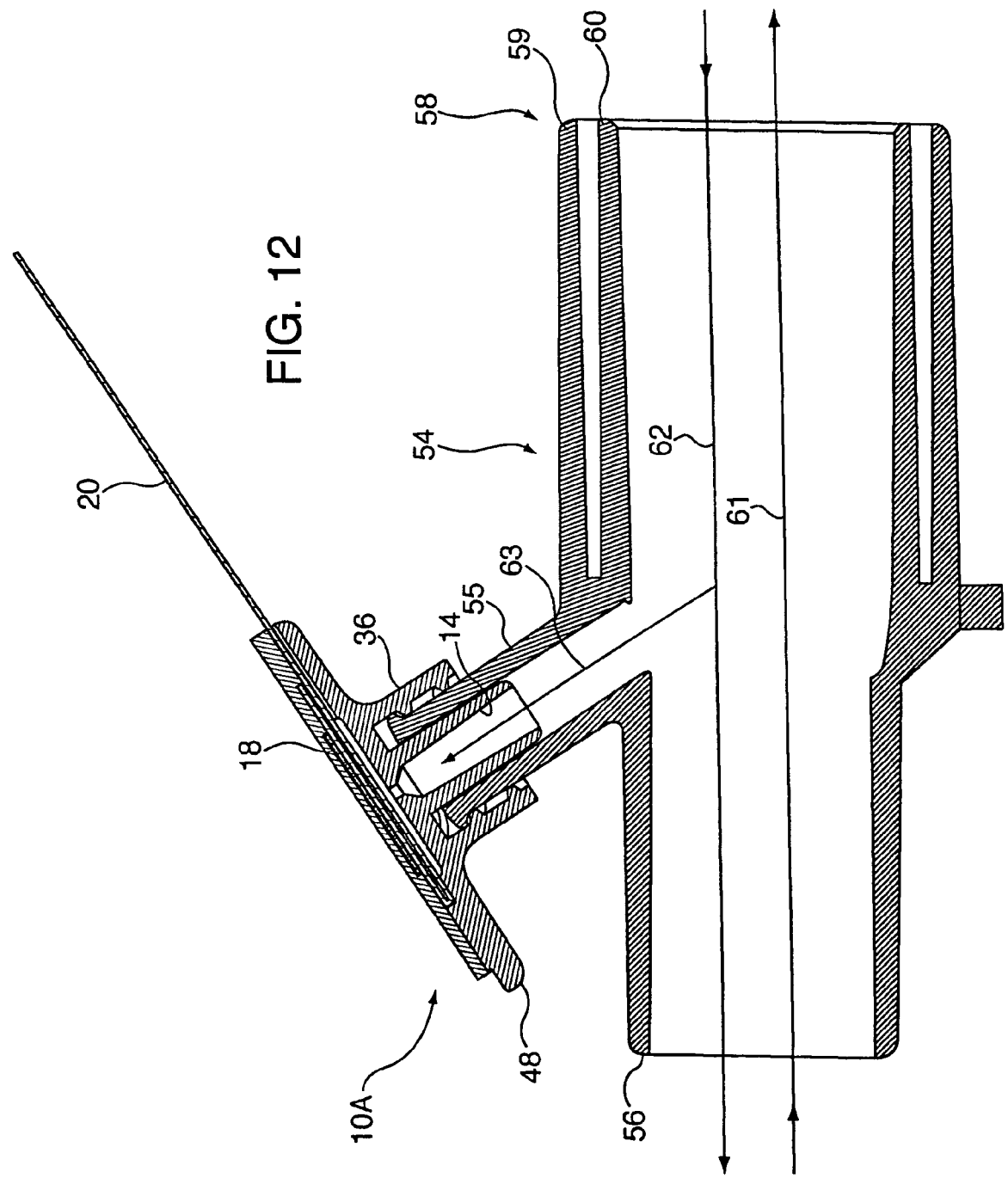
FIG. 12 is a vertical cross-sectional view of the embodiment of FIGS. 10 and 11.

Referring to FIGS. 10-12, a further embodiment of the present invention includes the carbon dioxide indicating apparatus 10A in combination with the tubular member indicated by general numerical designation 54. The tubular member 54 is provided with a locking female luer 55 extending outwardly therefrom at an acute angle A of about 45° (FIG. 10) with respect to the tubular member 54. The tubular end 56 of the tubular member 54, FIG. 12, may be suitably dimensioned for fluid-tight engagement with other devices, for example, the tubular connector 56 may be suitably dimensioned for insertion into and fluid-tight engagement with the patient port of a resuscitator. The opposite end of the tubular member 54 is indicated by general numerical designation 58 (FIG. 12) and will be understood to comprise two concentric tubular members 59 and 60. The concentric tubular members 59 and 60 may be suitably dimensioned for fluid-tight engagement with other devices, for example, the tubular member 60 may be suitably dimensioned for receiving the proximal end of an endotracheal tube in a fluid-tight engagement. The outer concentric tubular portion 59 may be suitably dimensioned for placement in fluid-tight engagement with a resuscitation mask. In operation, and by way of example, the embodiment of FIG. 12 upon being connected to the patient port of the resuscitator and the proximal end of an endotracheal tube as described above will have inhalation gas from the resuscitator flow through tubular member 54 and the endotracheal tube and into the patient's trachea in a direction opposite to the arrow 61 shown in FIG. 12 and upon the endotracheal tube being properly placed in the patient's trachea, the patient's exhalation gas including carbon dioxide will flow through the apparatus of FIG. 12 as indicated by the arrow 62 and a portion of such carbon dioxide containing gas as indicated by the arrow 63 will flow through the locking female luer 55 and, upon the activation pull tab 20 being removed as described above, will engage, and the carbon dioxide will react with, the carbon dioxide indicating material 18 which upon being calorimetric carbon dioxide indicating material will change color in response to the carbon dioxide and provide a visible indication thereof visible through the carbon dioxide indicating apparatus 10A in the manner also described above. Upon the connector end 56 of the tubular member 54 of FIG. 10 being connected to a resuscitator, and upon the connector end 58 being connected to an endotracheal tube intubating a patient, it will be understood that the angularity of the locking female luer 55 will enhance the ability of the operator of the resuscitator to see the top surface of the carbon dioxide indicating apparatus 11A, and the colors and carbon dioxide concentration indications, because such operator will be generally viewing such connection axially, that is, generally along the central axis of the tubular member 54. Were the locking female luer 55 to be oriented perpendicularly with respect to the tubular member 54, such operator upon viewing the above-noted connection axially would have a more difficult time in seeing the top surface of the carbon dioxide indicating apparatus 11A.

From FIGS. 10 and 11, it will be understood that the carbon dioxide indicating apparatus 10A is mounted to the female locking luer 55 provided angularly on the tubular member 54 by inserting the tubular member 14, male luer as noted above, into the locking female luer 55 as indicated by the arrow 63 and by rotating the apparatus 10A into threaded locking fluid-tight engagement with the female luer 55 by rotating the apparatus 10 as indicated by the arrow 64 in FIGS. 10 and 11. Rotation of the carbon dioxide indicating apparatus 10A causes the diametrically opposed, outwardly extending ridges or tabs 55a and 55b (FIG. 11) to threadedly engage the internal threads provided in the collar 36, as shown in FIG. 11, and pull the male luer 14 into slight interference sealing engagement with the female luer 55; manual rotation of the carbon dioxide indicating apparatus 10A is enhanced by the radially outwardly extending members 46-48 provided on the base disk 22, best seen in FIG. 11.

It will be understood that the combination invention embodiment shown in FIGS. 10-12, upon being connected to the resuscitator and endotracheal tube as described above, is particularly useful for providing a visual indication to indicate whether or not such endotracheal tube is correctly positioned in a patient's trachea and not incorrectly positioned in a patient's esophagus. Exhalation gas, as described generally above, from the patient's trachea contains sufficient carbon dioxide to provide the visual indication while exhalation gas from the patient's esophagus does not contain sufficient carbon dioxide to activate the carbon dioxide indicating material with the absence of such visual indication being a determination that such endotracheal tube has been incorrectly placed in a patient's esophagus.

Figure 13:
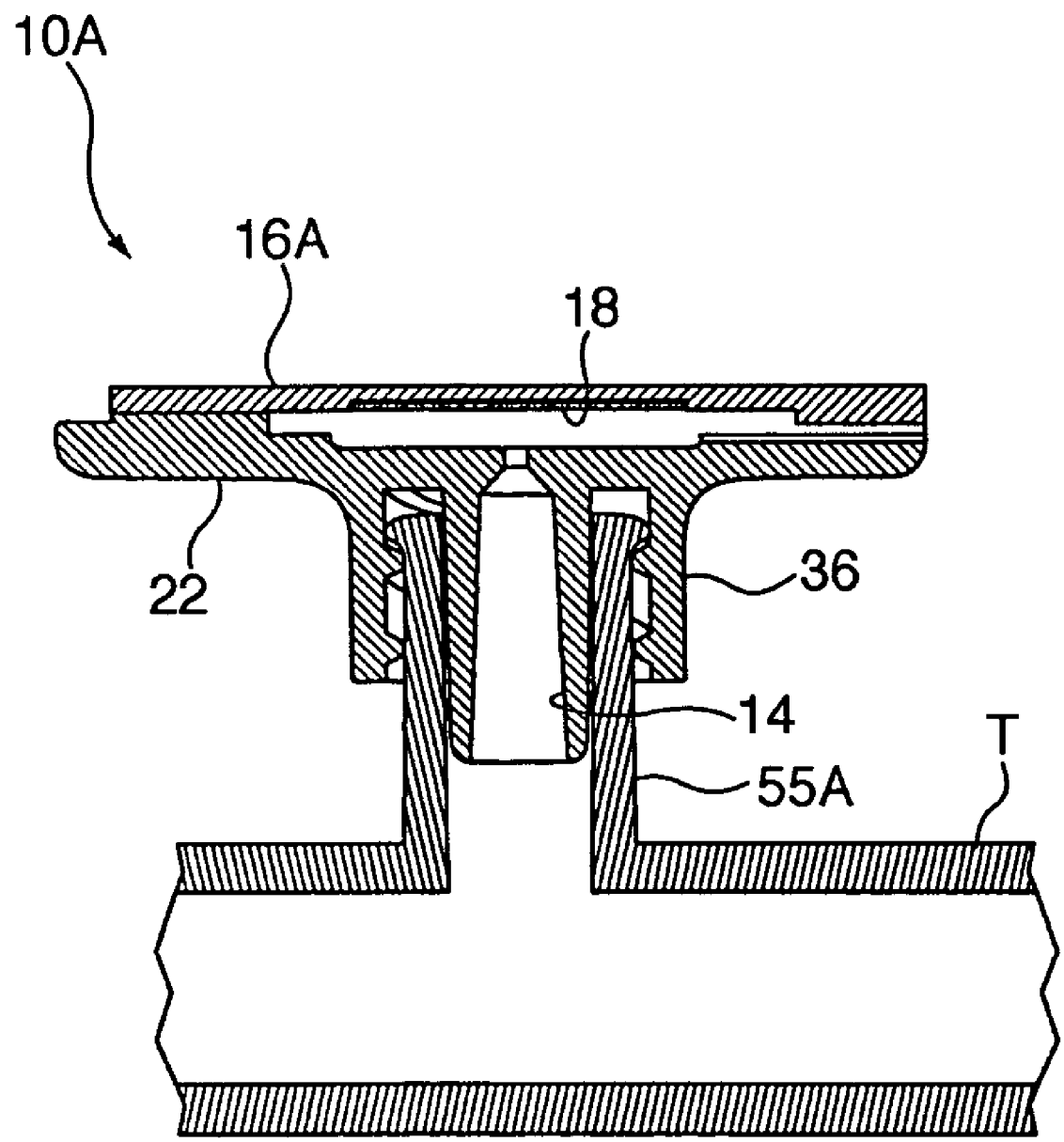
FIG. 13 is a vertical cross-sectional view of the carbon dioxide indicating apparatus embodiment of FIG. 12 with the activation pull tab removed.

Prior to describing the further combination embodiments of the present invention shown in FIGS. 14-19, reference is made to FIG. 13 and to the representative female locking luer 55A shown extending perpendicularly upwardly from the representative tubular member T. The locking female luer 55A rotatably engages the carbon dioxide indicating apparatus 10A in a fluid-tight sealing engagement the same as the angularly disposed locking female luer 55 engages the carbon dioxide indicating apparatus 10A in FIG. 12 and described above. In some of the embodiments shown in FIGS. 14-19, the locking female luer 55A is not shown, but it will be understood that each of the tubular members shown in these additional FIGS. is provided with the perpendicular upwardly extending female locking luer 55A shown in FIG. 13. It will be further understood from FIG. 13 as being representative of the additional embodiments shown in FIGS. 14-19 that the activation pull tab 20 (FIG. 12) has been removed to activate the carbon dioxide indicating material 18 (FIG. 12) and that, in these additional embodiments, the carbon dioxide indicating material 18 is the above-noted colorimetric carbon dioxide indicating material for providing a change in color as a visible indication of the presence of carbon dioxide.

Figure 14:
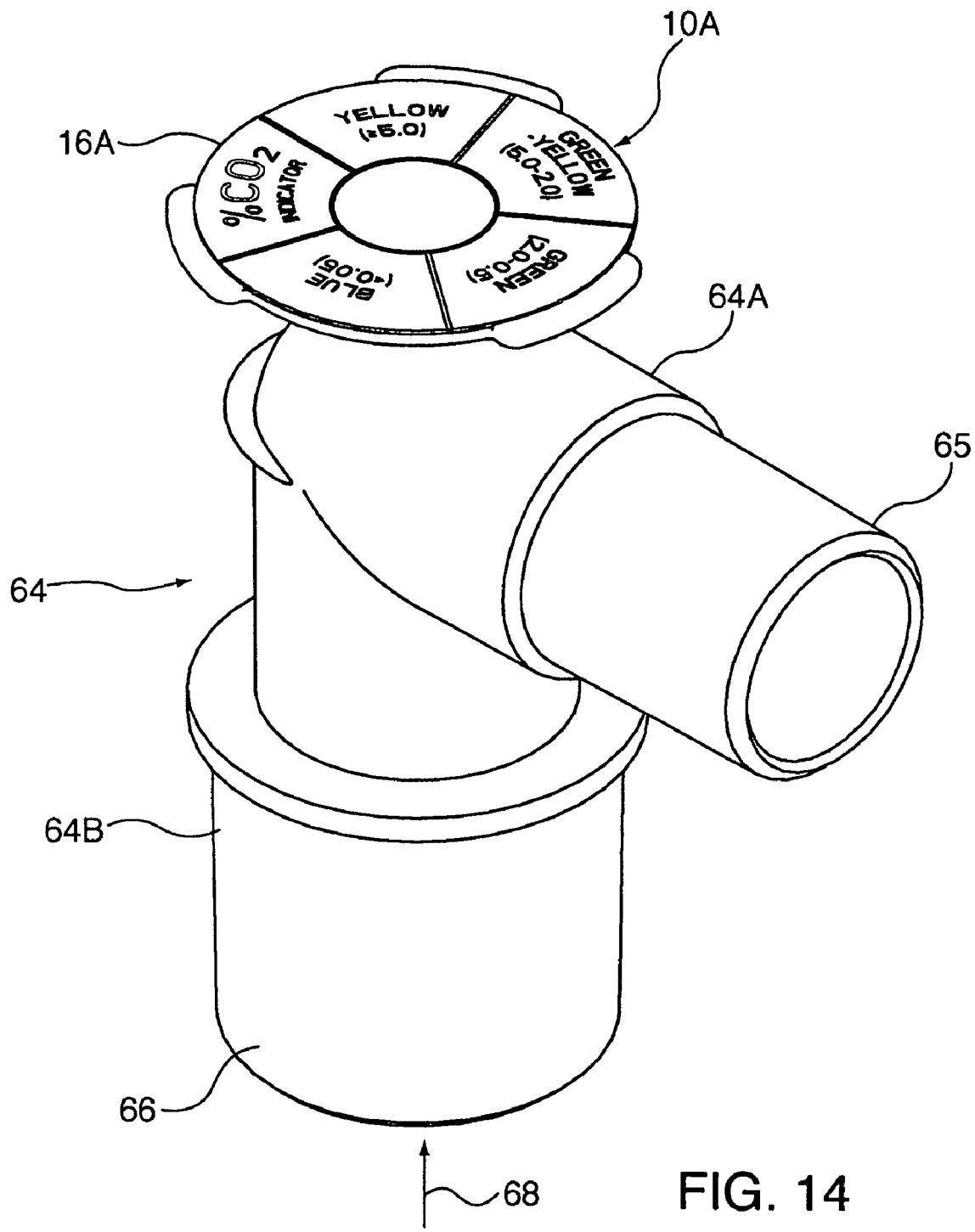
FIG. 14 is a perspective view of a fourth embodiment of carbon dioxide indicating apparatus embodying the present invention.

Referring specifically to FIG. 14, the combination embodiment of the present invention illustrated in FIG. 14 includes the carbon dioxide indicating apparatus 10A and the tubular member indicated by general numerical designation 64. The tubular member 64 may be a female luer-ported elbow tubular member including a first tubular member 64A and a second tubular member 64B and further including a tubular connector end 65 suitably dimensioned for fluid-tight engagement with, for example, a breathing circuit and also including tubular connector end 66 suitably dimensioned for fluid-tight engagement with, for example, a mask connector or the proximal end of an endotracheal tube. Upon carbon dioxide containing gas indicated by the arrow 68 flowing into the tubular member 64, a portion of the gas will enter the locking female luer extending upwardly perpendicularly, not shown in FIG. 14 but understood to be the same as shown in FIG. 13, and such portion of the carbon dioxide indicating gas 68 will enter the carbon dioxide indicating apparatus 10A and produce a color change visible through the cover disk 16A of the carbon dioxide indicating apparatus 11A. It will be understood that the combination embodiment shown in FIG. 14 is particularly useful for the purpose of verifying proper endotracheal tube placement and indication of continuing effective ventilation.

Figure 15:
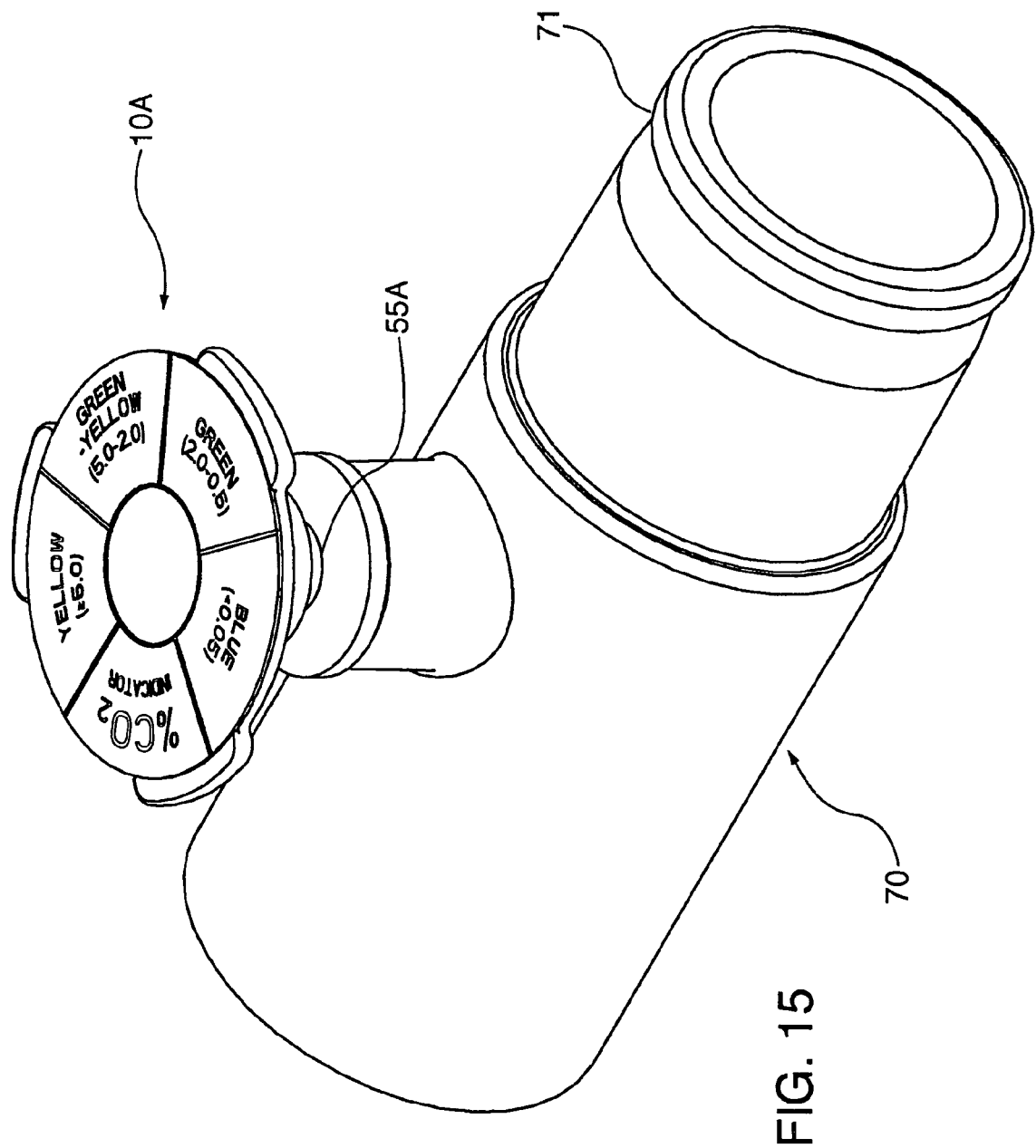
FIG. 15 is a perspective view of a fifth embodiment of carbon dioxide indicating apparatus of the present invention.

The further embodiment of the present invention shown in FIG. 15 includes the carbon dioxide indicating apparatus 10A and a tubular member indicated by general numerical designation 70 which may be a female luer-ported machine cuff such as for example the tubular machine cuff or connector typically extending outwardly from a ventilator or an anesthesia machine in both the expiratory and inspiratory limbs of a patient breathing circuit. For example, upon the machine cuff embodiment shown in FIG. 15 being in the expiratory limb of the breathing circuit through which exhalation gas from the patient flows, and returns to the machine, the tubular member or machine cuff 70 will include a cylindrical connector end 71 suitably dimensioned for fluid-tight engagement with a hose connected to, for example, an endotracheal tube. In this expiratory limb, the carbon dioxide indicating apparatus 10A by indicating the presence of carbon dioxide will provide a verification of proper endotracheal tube placement and provide an indication of continuing effective ventilation. Upon the machine cuff or tubular member 70 being connected in the inspiratory limb of the breathing circuit, as is known to the art, such inspiratory limb may include a carbon dioxide absorber for absorbing carbon dioxide which undesirably may be in ventilation or anesthesia gas going to the patient. In such inspiratory limb embodiment, the carbon dioxide indicating apparatus 10A will provide an indication of the effectiveness of such carbon dioxide absorber. Such carbon dioxide absorber is taught at lines 18-35 in column 1 of the above-incorporated U.S. Pat. No. 2,890,177.

Figure 16:
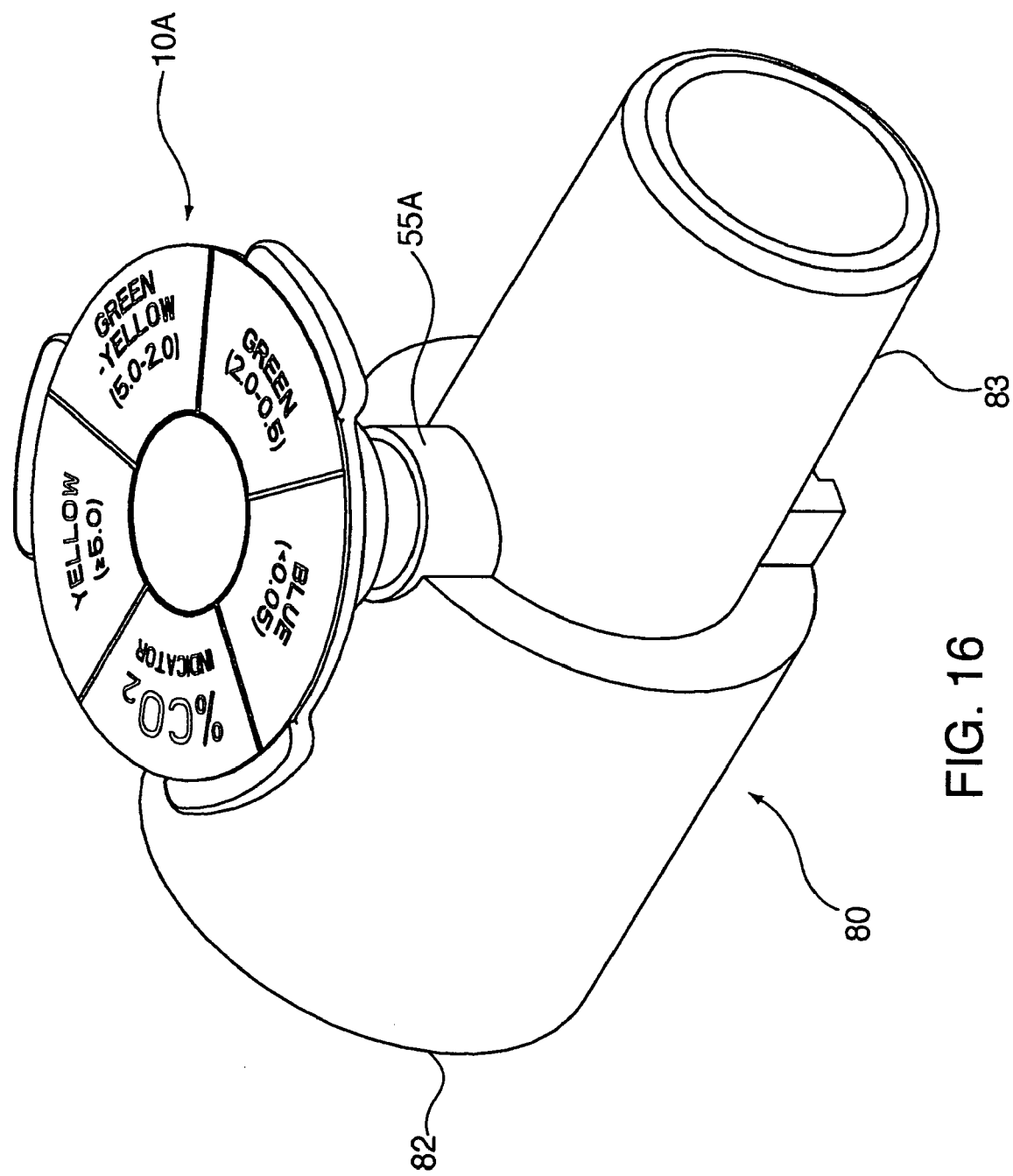
FIG. 16 is a sixth embodiment of carbon dioxide indicating apparatus of the present invention.

FIG. 16 illustrates a further combination embodiment of the present invention including the carbon dioxide indicating apparatus 10A and the tubular member indicated by general numerical designation 80 which may be a straight-female luer fluid connector sometimes referred to in the art as a gas-sampling tee. The tubular connector end 82 is dimensioned for fluid-tight engagement with, for example, a patient connector or wye and the tubular connector end portion 83 is dimensioned for fluid-tight engagement with a patient port or wye or the expiratory limb of a breathing circuit. Upon the connector end 82 being connected to an endotracheal tube intubating a patient, and upon the patient exhaling through such endotracheal tube and the patient's exhalation gas flowing through the tubular member 80, a portion is diverted through the upwardly perpendicularly extending female locking luer 55A and into the carbon dioxide indicating apparatus 10A to provide the visual indication described above and thereby providing verification of proper endotracheal tube placement and a further indication of continuing effectiveness of patient ventilation in a ventilator embodiment.

Figure 17:
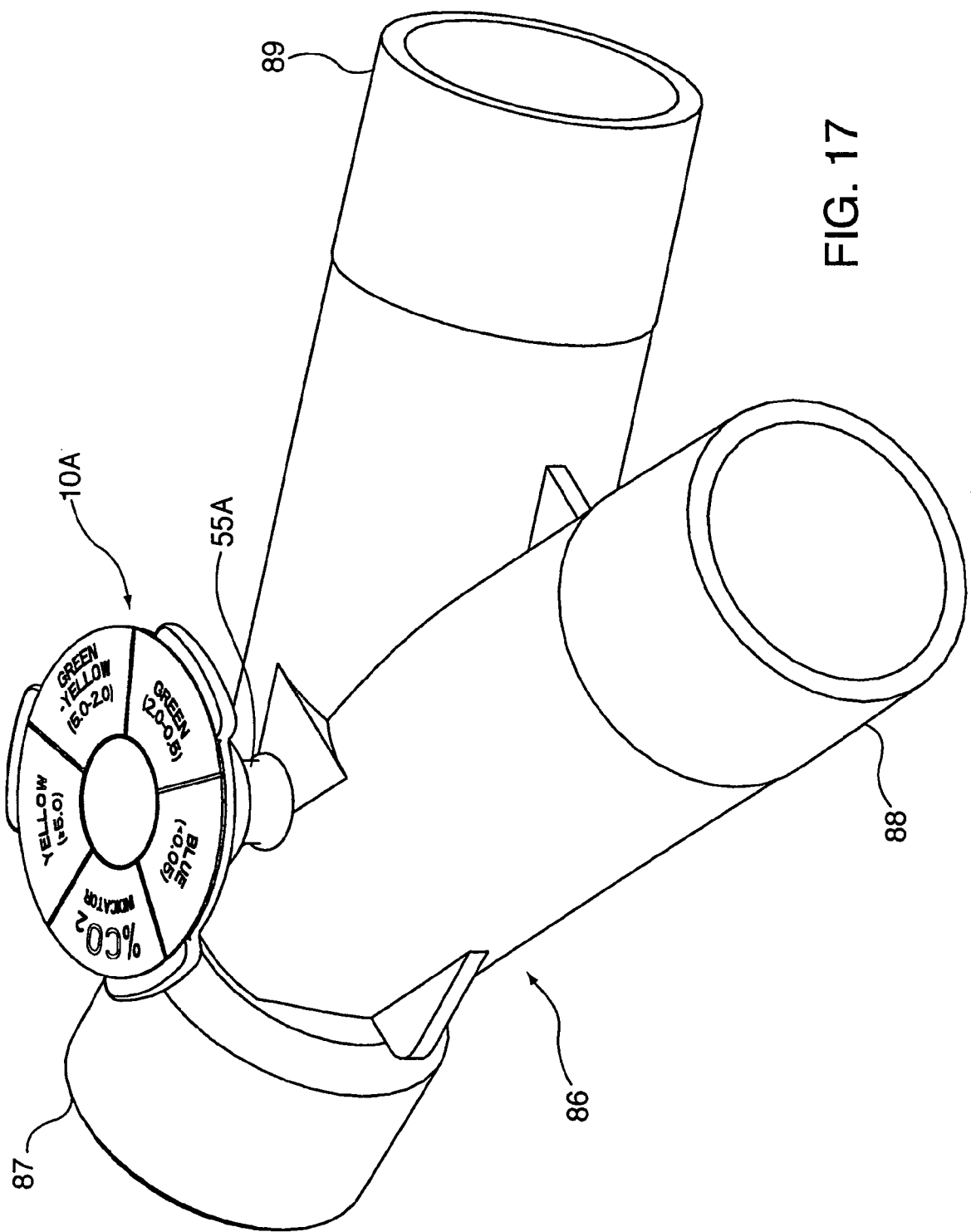
FIG. 17 is a seventh embodiment of carbon dioxide indicating apparatus of the present invention.

Yet another combination embodiment of the present invention is illustrated in FIG. 17 and includes the carbon dioxide indicating apparatus 10A and a tubular member indicated by general numerical identification 86, which in this embodiment is a female luer-ported wye or bifurcated wye. The tubular member 86 includes a perpendicularly upwardly extending female locking luer 55A for fluid-tight engagement with the locking male luer provided on the apparatus 10A as illustrated and described in connection with FIGS. 10-12, and a tubular connector end 87 dimensioned for fluid-tight engagement with a patient port such as an endotracheal tube intubating a patient, a tubular connector end 88 dimensioned for fluid-tight engagement with the expiratory limb of a breathing circuit and a tubular connector end 89 dimensioned for fluid-tight engagement with the inspiratory limb of a breathing circuit. Again, upon exhalation gas from a patient containing carbon dioxide flowing from the endotracheal tube and through the tubular member 86, a portion is diverted into the carbon dioxide indicating apparatus 10A to provide the above-described colorimetric carbon dioxide indication thereby providing verification of proper endotracheal tube placement and a further indication of continuing effectiveness of the ventilation in a ventilator embodiment.

Figure 18:
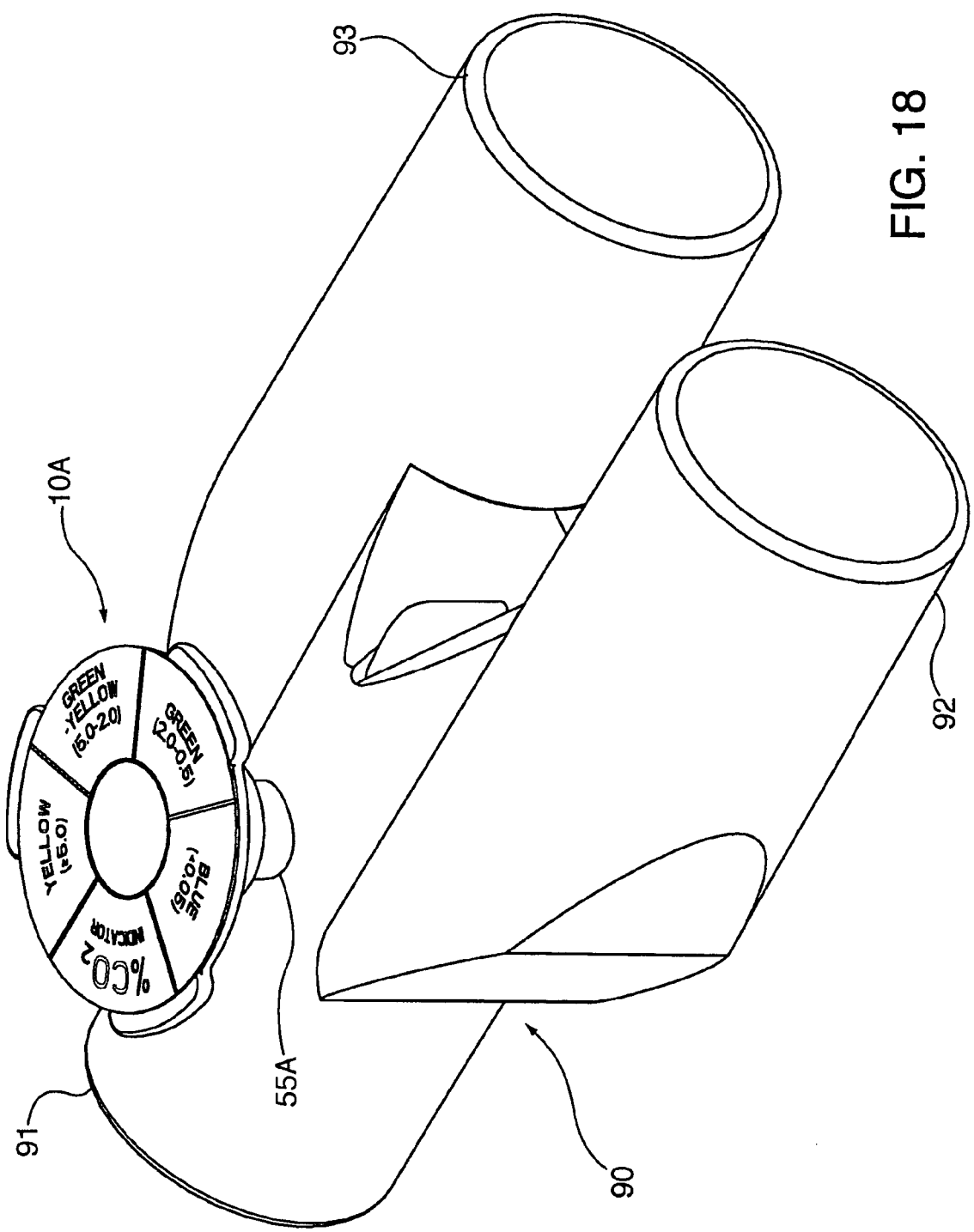
FIG. 18 is an eighth embodiment of carbon dioxide indicating apparatus of the present invention.
Figure 19:
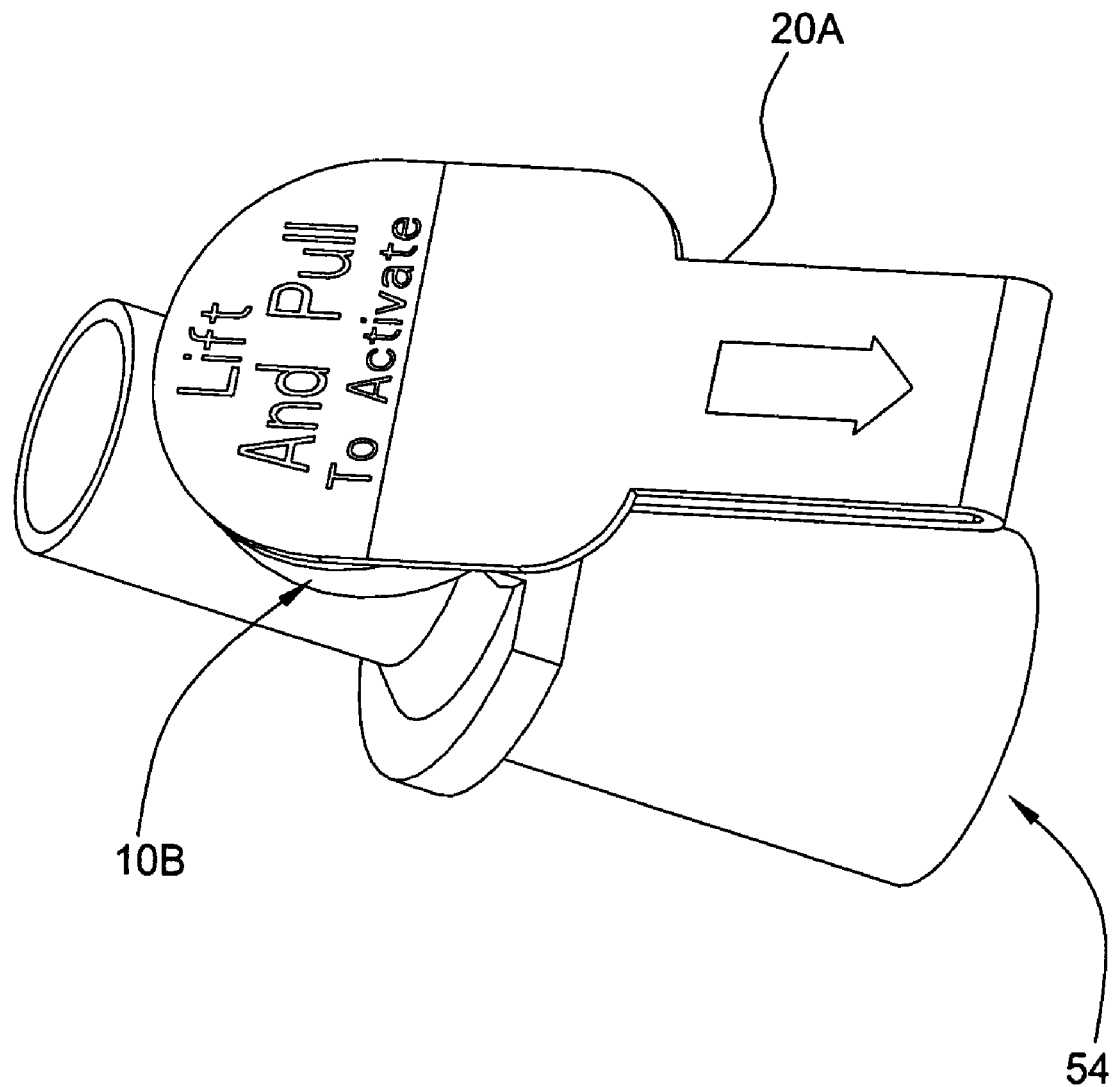
FIG. 19 is a top perspective view of a ninth embodiment of carbon dioxide indicating apparatus of the present invention.

The last combination embodiment of the present invention is shown in FIG. 18 and includes the carbon dioxide indicating apparatus 10A and the tubular member indicated by general numerical designation 90. The tubular member 90 is of the type typically referred to in the art as a female luer ported wye or parallel-wye. The tubular member 90 includes a tubular connector end 91 dimensioned for fluid-tight engagement with a patient port such as provided on an endotracheal tube, a tubular connector end 92 is suitably dimensioned for fluid-tight engagement with the expiratory limb of a breathing circuit and a tubular connector end 93 is dimensioned for fluid-tight engagement with the inspiratory limb of a breathing circuit. The tubular member 90 is provided with a perpendicularly upwardly extending female locking luer 55A for fluid-tight engagement with the carbon dioxide indicating apparatus 10A as shown in FIG. 13 and described above. Accordingly, upon a patient's exhalation gas containing carbon dioxide flowing from the endotracheal tube and through the tubular member 90, a portion is diverted into the carbon dioxide indicating apparatus 10A to provide a visual indication thereof such as the above-described colorimetric visual indication. Such calorimetric visual indication will provide a verification of the proper placement of such endotracheal tube and an indication of continuing effective ventilation in a ventilator embodiment.

Referring again to FIGS. 2 and 8, it will be understood that the carbon dioxide indicating material 18 may be shaped other than as a disk, for example, the carbon dioxide indicating material 18 may be rectangular, octagonal and the like and, it will be further understood that in such event the recess 24 shown in the embodiment of FIG. 4, will be of a suitable complementary shape.

Referring again to the carbon dioxide indicating apparatus 10 and 10A of the present invention, it will be further understood that upon the carbon dioxide indicating material 18 being the above-noted calorimetric carbon dioxide indicating material available from BreGas AB, and such carbon dioxide indicating apparatus being connected in a patient's breathing circuit through which the patient's exhalation gas containing carbon dioxide flows, such carbon dioxide indicating material 18 will alter its color in pace with the breathing pattern of the patient according to: blue-green-yellow-green-blue-green-yellow-green-blue, etc. and thus the carbon dioxide indicating apparatus according to the invention will be further understood to be useful as a general breathing monitor as well as an endotracheal tube intubation monitor.

Referring to FIGS. 19-24, there is shown a further embodiment of carbon dioxide indicating apparatus embodying the present invention and indicated by general numerical designation 10B. Carbon dioxide indicating apparatus 10B is for use with carbon dioxide indicating material of the type described above in the BACKGROUND OF THE INVENTION which experiences degradation upon exposure to ultraviolet radiation, such ultraviolet radiation degradable carbon dioxide indicating material is shown diagrammatically in FIG. 21 and identified by numerical designation 18A. With the exception of the activation pull tab, or elongated removable blocking member 20B, carbon dioxide indicating apparatus 10B is the same as the carbon dioxide indicating apparatus 10 shown in FIGS. 1-6 and described above. Further, in this additional embodiment, the carbon dioxide indicating apparatus 10B is shown attached to the tubular member 54 shown in FIGS. 10-12 and described above. It will be understood that components or elements comprising the carbon dioxide indicating apparatus 10B which are the same as the components of the carbon dioxide indicating apparatus 10 are given the same numerical designations and it will be understood to perform the same functions, the same with regard to the tubular member 54 shown in FIGS. 10-12. It will be noted particularly from FIGS. 21, 22 and 23 that the carbon dioxide indicating apparatus 10B includes the circular disk member 12 shown in FIG. 1 and described above.

Figure 20:
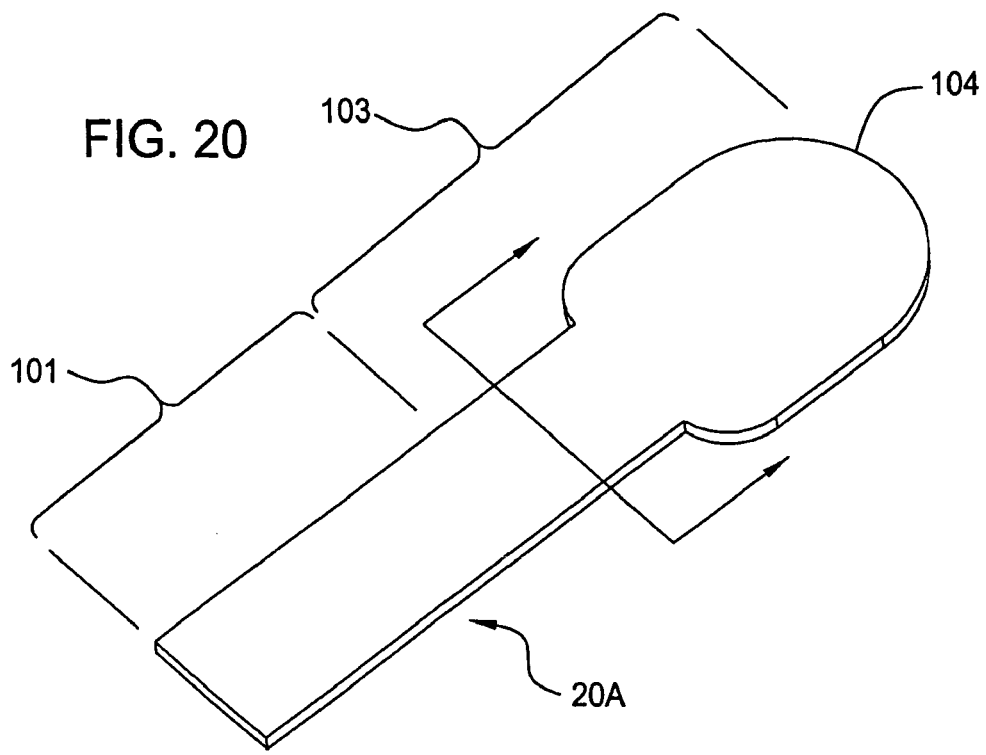
FIGS. 20, 20A and 20B are diagrammatical illustrations of the structure of a removable foldable elongated blocking member of the ninth embodiment.

Activation pull tab or removable elongated foldable blocking member 20A is shown in perspective in FIG. 20. Blocking member 20A includes a first end portion 101 and a second end portion 103. It will be understood that the first end portion 101 may have the same structure and perform the same function as the activation pull tab 20 shown in FIGS. 1-6 and described above, namely, the first end portion of the activation pull tab 101 is, as shown in FIG. 4 and described above, for initially overlying and blocking the internal passageway 15 of the tubular member 14 thereby preventing the carbon dioxide indicating material 18, 18A of FIG. 21 in this embodiment, from being in fluid communication with the carbon dioxide containing gas 44. In addition, the first end portion 101 of the blocking member 20A is also for initially extending through the radial slot 26 (FIG. 4) and sealing such radial slot, and radial slot 34, and thereby preventing the carbon dioxide indicating material 18, 18A of FIG. 21 in this embodiment, from being in fluid communication with the atmosphere.

Figure 20A:
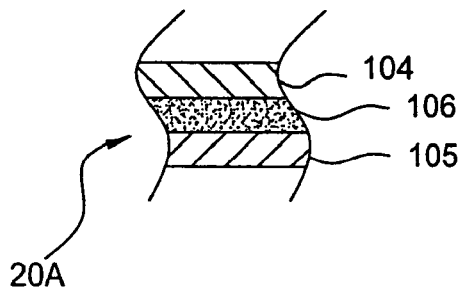
Figure 20B:
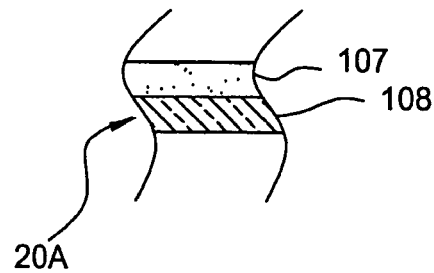

Referring again to FIG. 20, it will be understood that the second end portion 103 of the blocking member 20A is for initially shielding carbon dioxide indicating material 18A from ultraviolet radiation. More particularly, as shown in FIG. 22 and illustrated diagrammatically in FIG. 21, the second end portion 103 of the blocking member 20A is for being folded back upon itself in U-shaped fashion to cover the circular disk member 12 and initially shield the carbon dioxide indicating material 18A from ultraviolet radiation. As illustrated diagrammatically in FIG. 20A, the blocking member 20A may include a layer of polyester 104 laminated to a layer of metal foil 105 by a suitable adhesive 106 or, as illustrated diagrammatically in FIG. 20B, the blocking member 20A may be a metallized layer of polyester such as the layer of polyester 107 to which a metallized layer 108 has been suitably deposited. The layer of metal foil 105 in FIG. 20A and the metallized layer 108 in FIG. 20B will reflect ultraviolet radiation and thereby shield, or initially shield, the carbon dioxide indicating material 18A of FIG. 21 from such ultraviolet radiation. It will be further understood, and referring again to FIG. 20, that only the second end portion 103 of the blocking member 20A may have the structure illustrated diagrammatically in FIG. 20A or 20B, and that the first end portion 101 may merely be a layer of polyester, or other suitable material suitably connected to the second end portion 103. It will be further noted from FIG. 20 that the first end portion 101 of the blocking member 20A is generally rectangular and that the outer portion of the second end portion 103 is an enlarged generally circular portion 104 generally complementary in size and shape to the circular disk member 12 comprising the carbon dioxide indicating portion 10B. This complementary size and shape facilitates the coverage of the circular disk member 12 and initial ultraviolet radiation shielding of the carbon dioxide indicating material 18A, FIG. 21.

Figure 21:
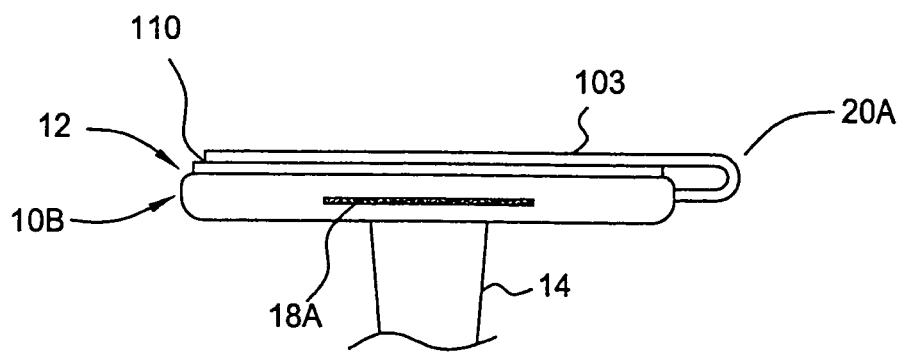
FIG. 21 is a diagrammatical illustration of initial ultraviolet shielding of carbon dioxide indicating material subject to degradation upon exposure to ultraviolet radiation.
Figure 22:
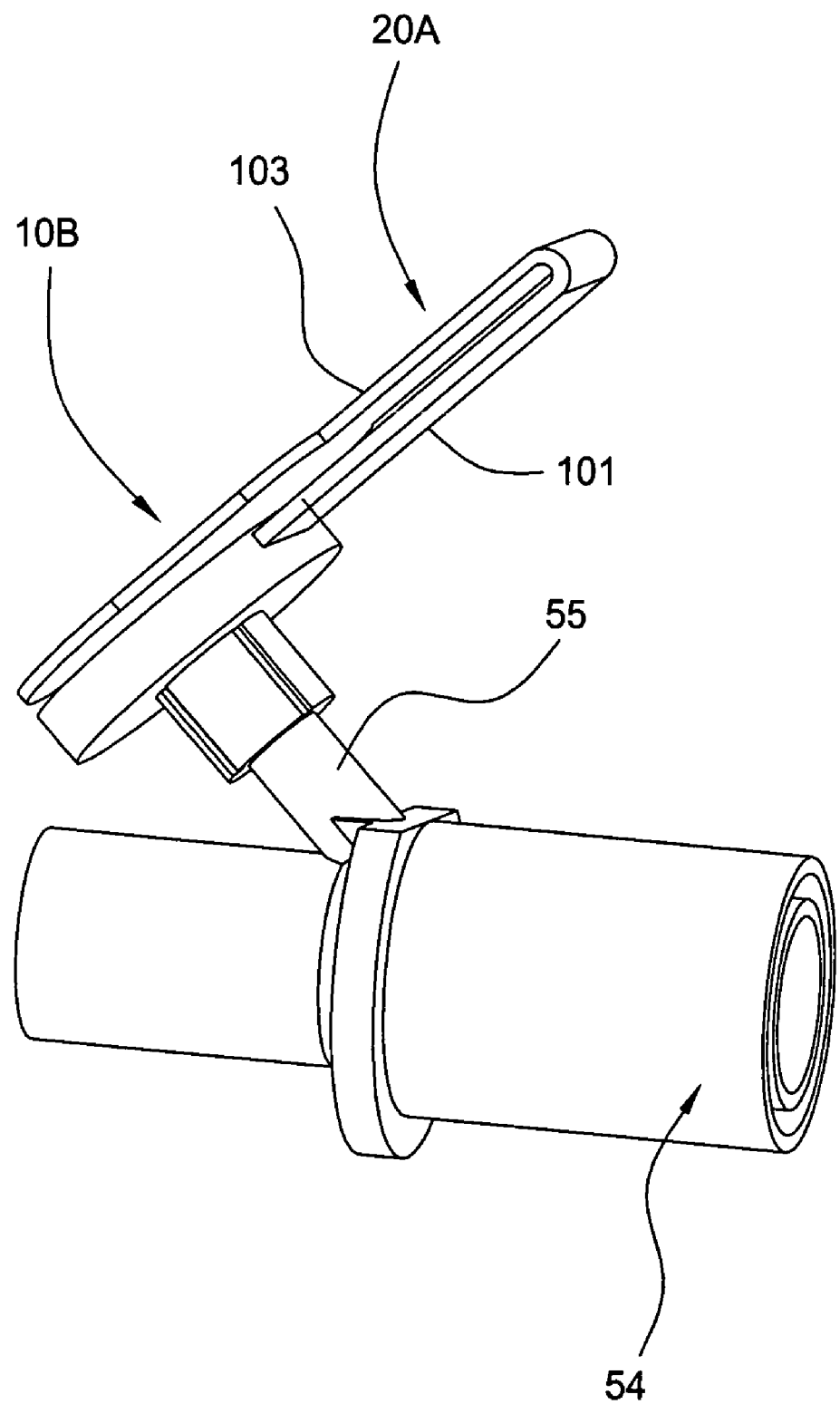
FIG. 22 is a side view of the carbon dioxide indicating apparatus shown in FIG. 19.

It will be further understood from FIG. 21 that in this further embodiment of the present invention the second end portion 103 of the removable elongated foldable blocking member 20A is for being folded over the carbon dioxide indicating apparatus 10B and removably adhered to the top surface of the apparatus 10B by a suitable adhesive 110. Accordingly, it will be understood that the second end portion 103 having either the UV shielding structure shown in either FIG. 20A or 20B will initially reflect, or at least substantially reflect, ultraviolet radiation and will therefore initially shield the carbon dioxide indicating material 18A, FIG. 21, from ultraviolet radiation.

Figure 23:
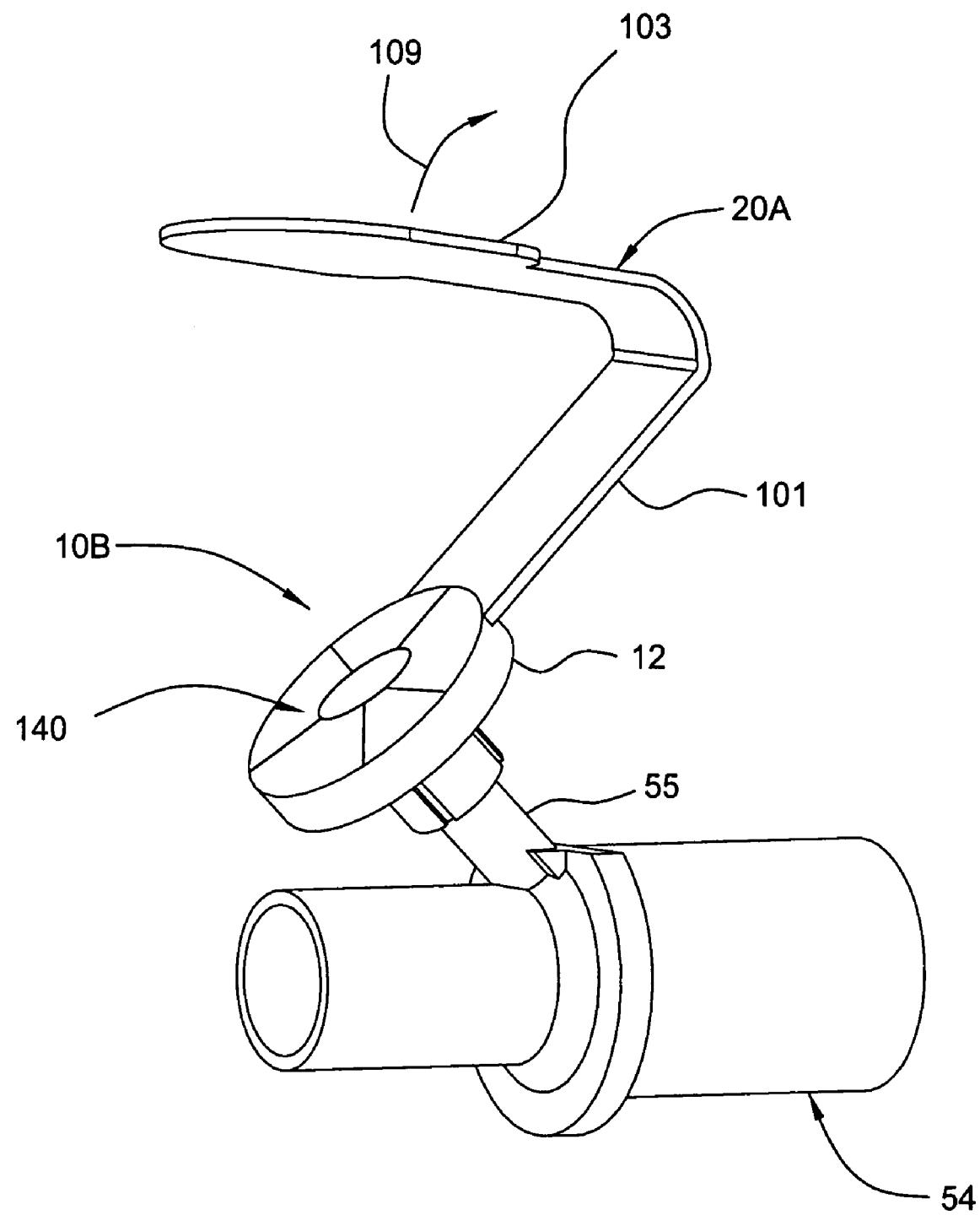
FIG. 23 illustrates the removal of the ultraviolet radiation shield of the initial ultraviolet radiation shielding.
Figure 25:
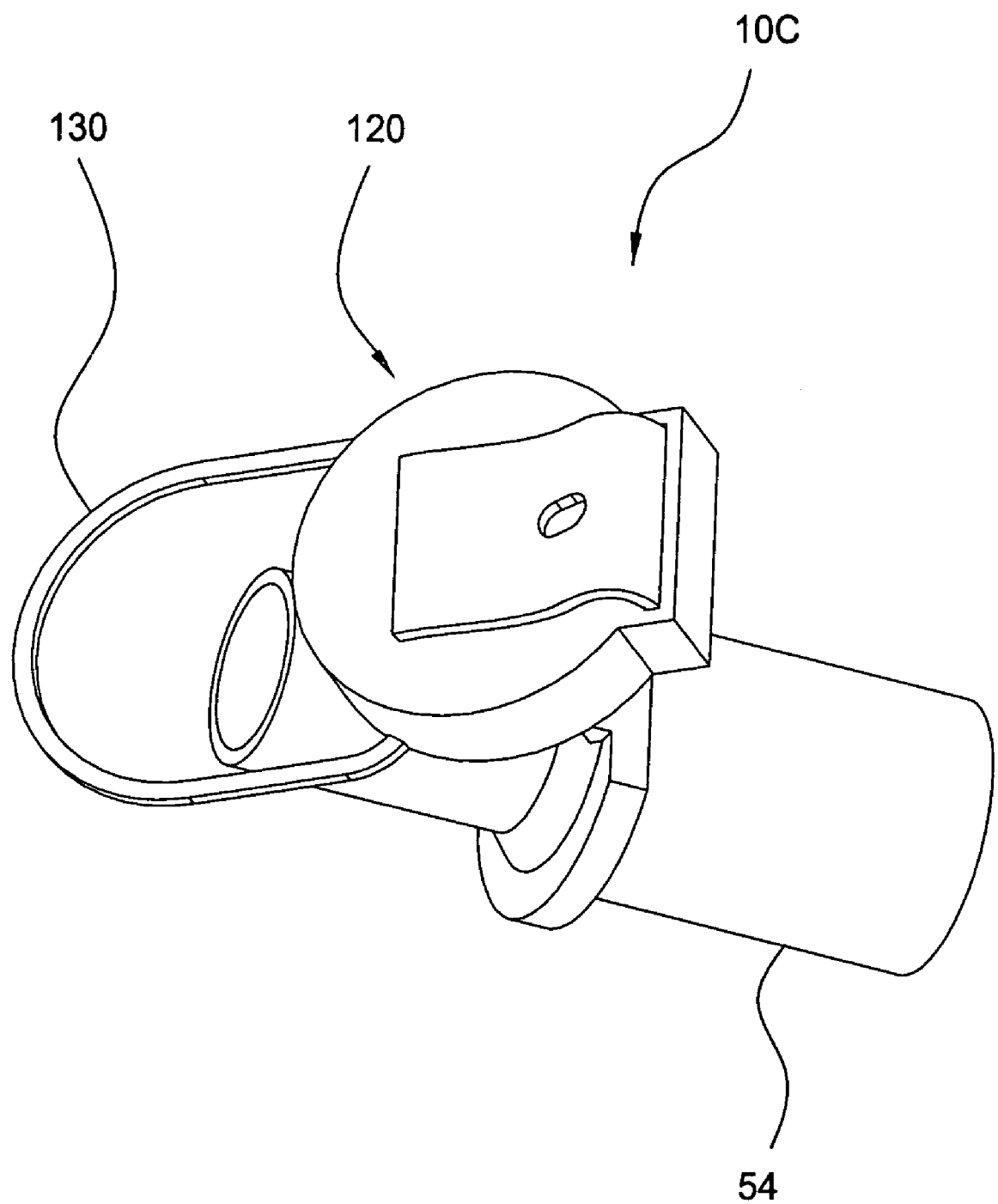
FIG. 25 is a perspective view of a tenth embodiment of carbon dioxide indicating apparatus of the present invention.

In use, as illustrated in FIG. 23, the second end portion 103 of the removable elongated foldable member 20A is manually lifted off of the carbon dioxide indicating apparatus 20B, as indicated by the curved arrow 109, to expose the carbon dioxide indicating material 18A and the carbon dioxide percentage indicating indicia shown in FIGS. 1 and 7, to view, and, as further illustrated in FIG. 24, the blocking member 20A is manually pulled outwardly as indicated by the straight arrow 111 to pull the first end portion 103, FIG. 20, of the blocking member 20A out of the carbon dioxide indicating apparatus 10B, i.e., to pull the first end portion 101 of the blocking member 20A from over the passageway 15 and out of the radial slot 26 shown in FIG. 4, to thereby place the carbon dioxide indicating material 18A, FIG. 21, in fluid communication with the carbon dioxide containing gas 44, FIG. 4, in the internal passageway 15, and to place the carbon dioxide indicating material 18A in fluid communication with the atmosphere. The carbon dioxide indicating apparatus 10B will thereafter function to indicate the presence of carbon dioxide as described above with regard to, for example, the carbon dioxide indicating apparatus 10 of FIGS. 1-6.

A still further embodiment of carbon dioxide indicating apparatus of the present invention is illustrated in FIGS. 25-33 and indicated by general numerical designation 10C. Carbon dioxide indicating apparatus 10C is also shown mounted to the tubular member 54. Carbon dioxide indicating apparatus 10C is the same as the carbon dioxide indicating apparatus 10B shown in FIGS. 19-24 except that the outer portion of the second end portion 103, of the removable blocking member 20A, FIG. 20, is provided with a removable cap indicated by general numerical designation 120.

Figure 27:
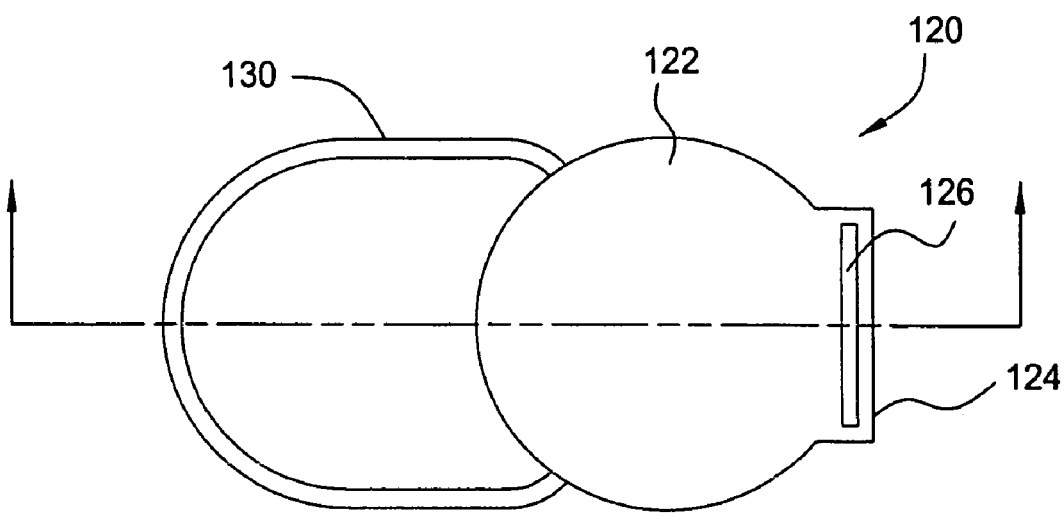
FIGS. 27-29 are detailed views of the removable cap of the tenth invention embodiment.
Figure 28:
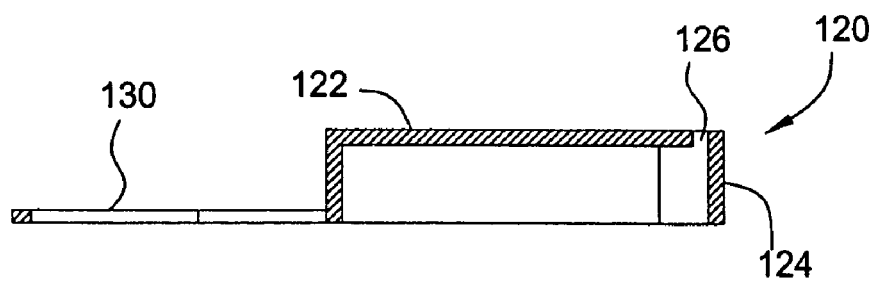
Figure 29:
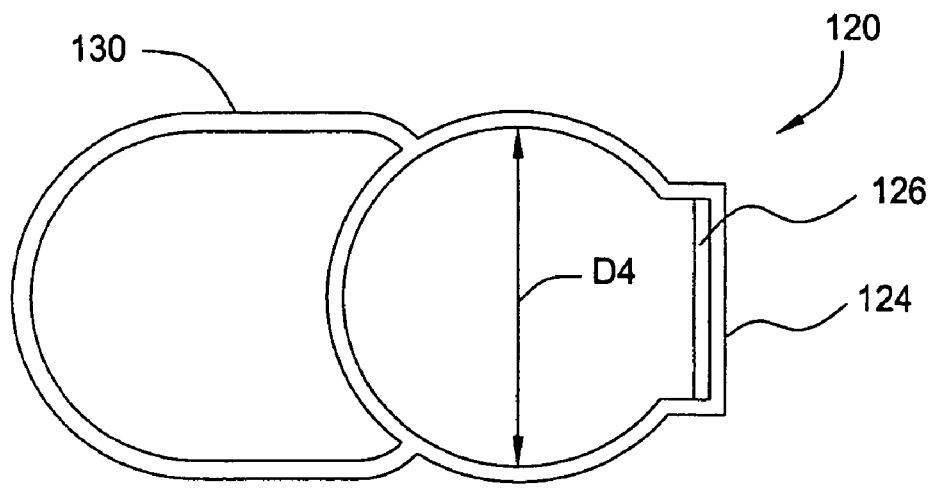
Figure 30:
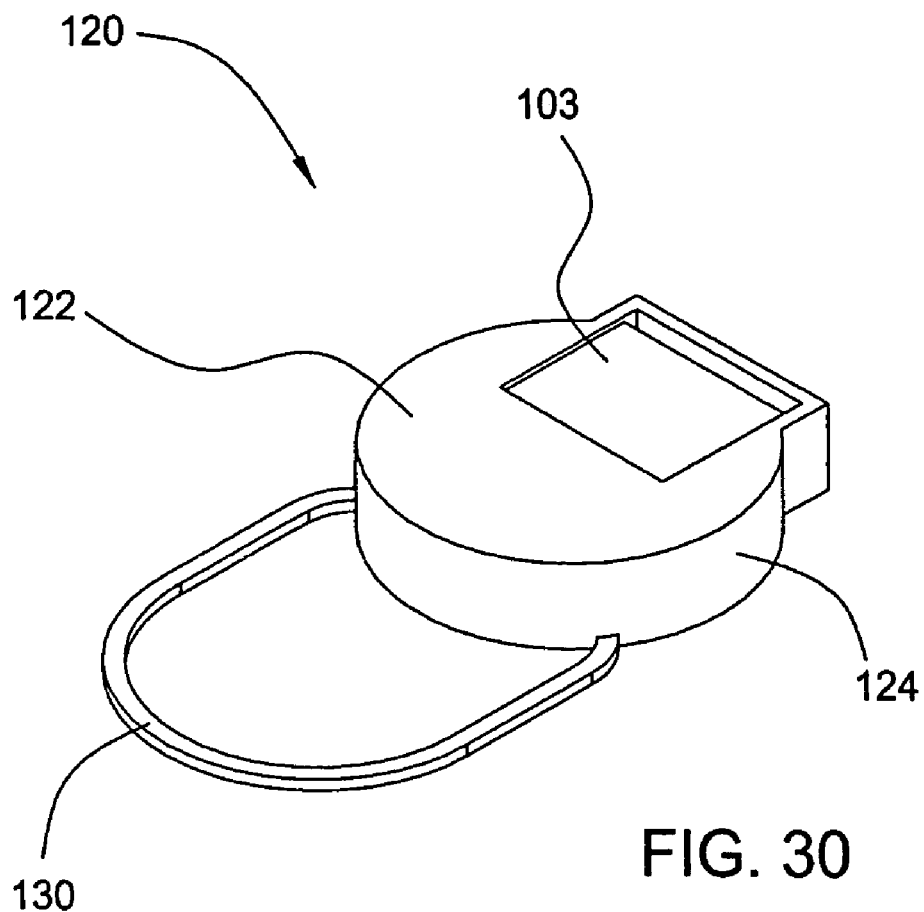
FIG. 30 is a perspective view of the removable cap.
Figure 31:
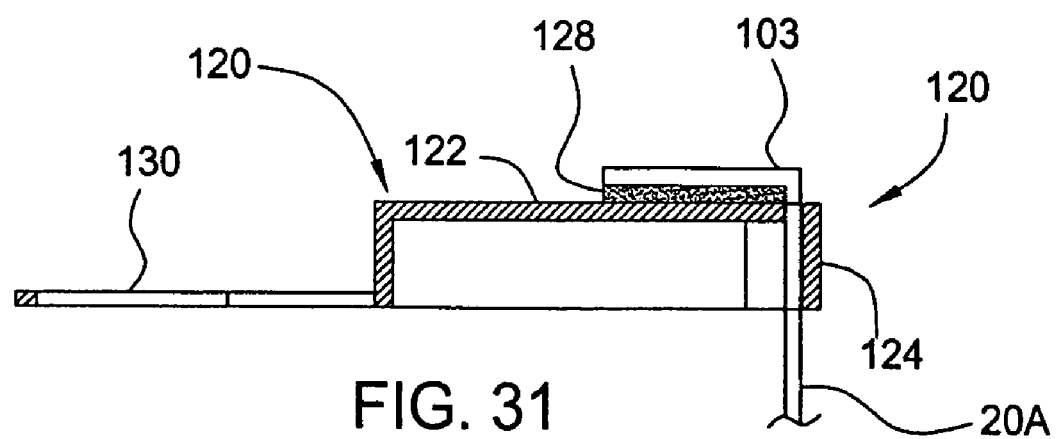
FIG. 31 is a diagrammatical view, in partial cross-section, showing the securing of one end of a removable foldable elongated blocking member to the top of the removable cap.

The removable cap 120, shown particularly in FIGS. 27-29, includes a generally circular top 122 having a generally straight rearward portion 124. As shown in FIG. 28, the top 122 is circumscribed by a generally perpendicularly downwardly extending peripheral wall 124 provided with an opening 126 extending therethrough. As will be understood from FIG. 31, the outer end portion 103 of the blocking member 20A extends through the opening 126 and is folded over the top 122 of the cap 120 and suitably secured thereto such as for example by a layer of suitable adhesive 128.

Figure 26:
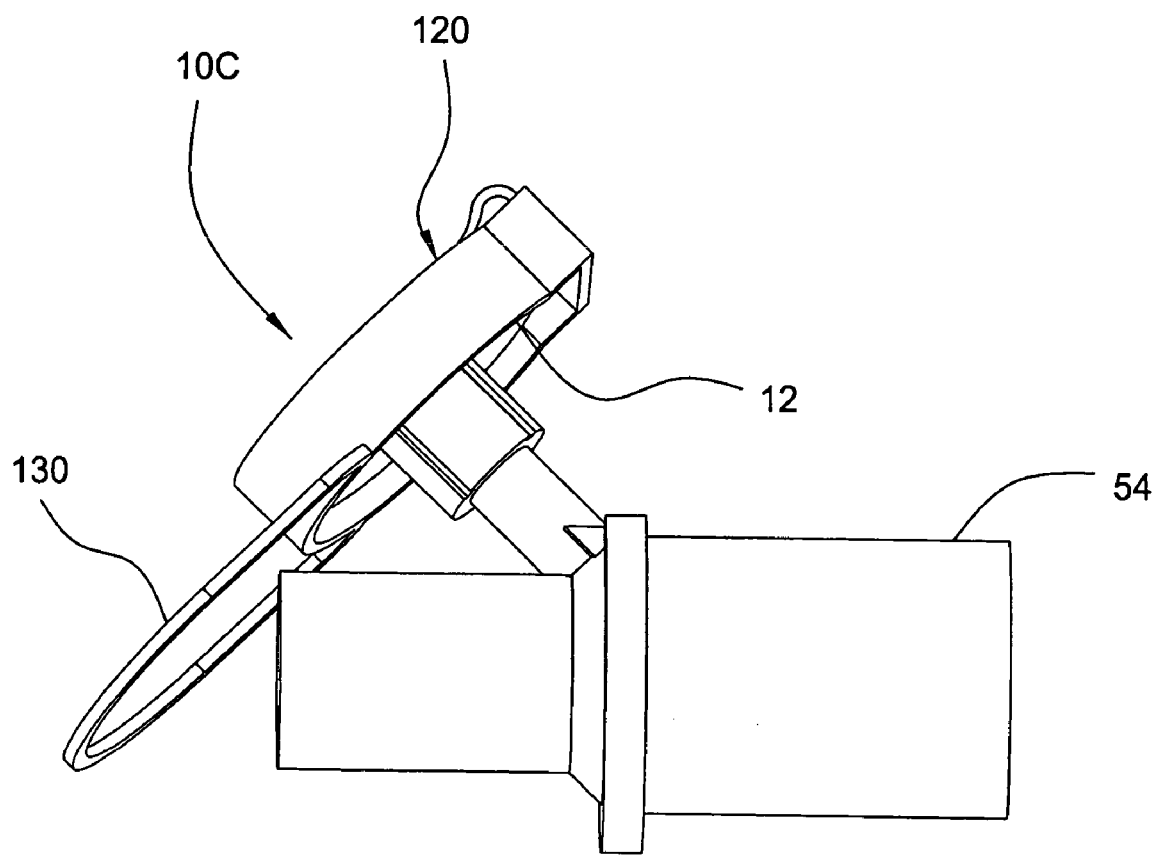
FIG. 26 is a side view of the embodiment shown in FIG. 25.
Figure 32:
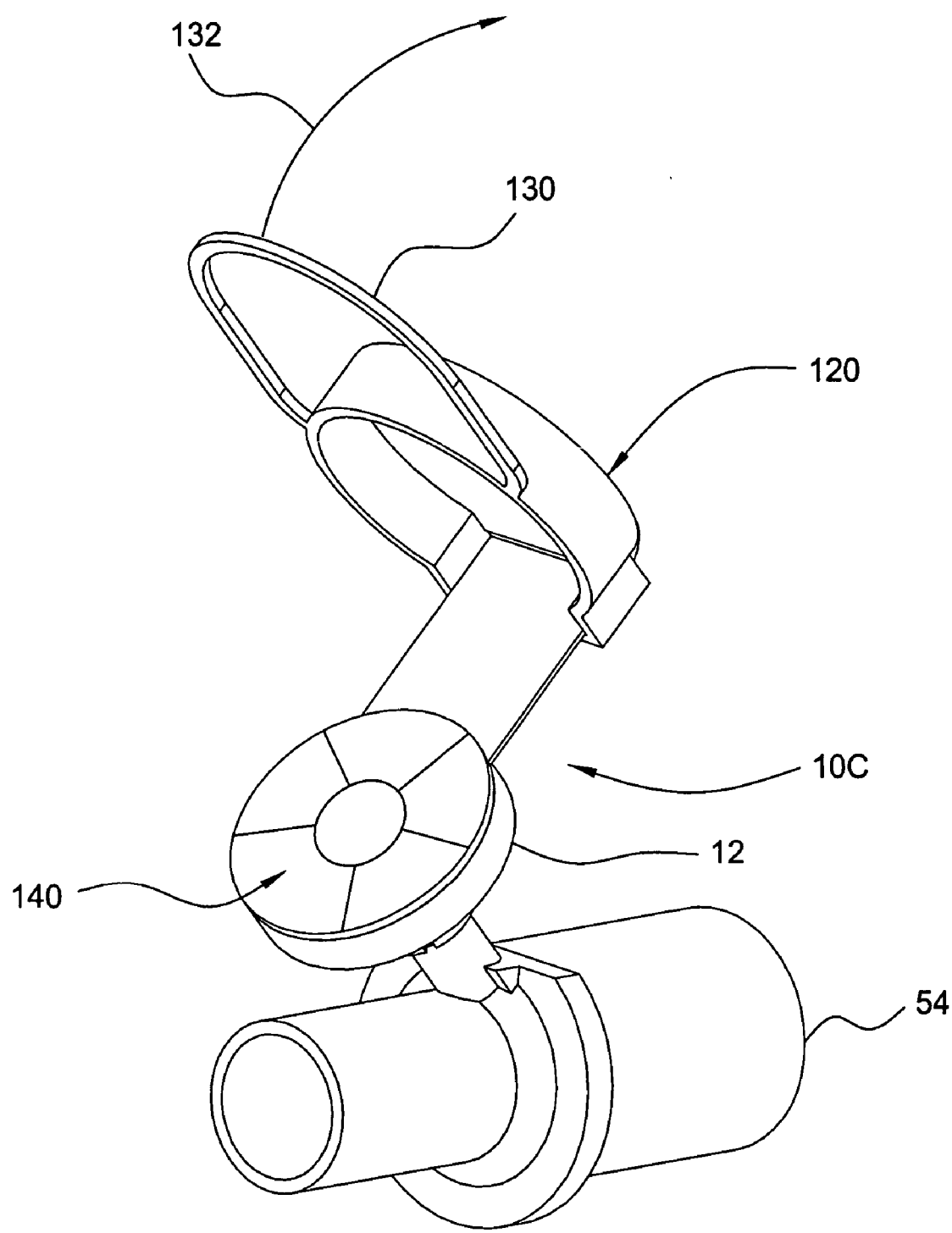
FIG. 32 is a diagrammatical illustration of the unsnapping and removing of the cap from the circular disk comprising the tenth invention embodiment.
Figure 33:
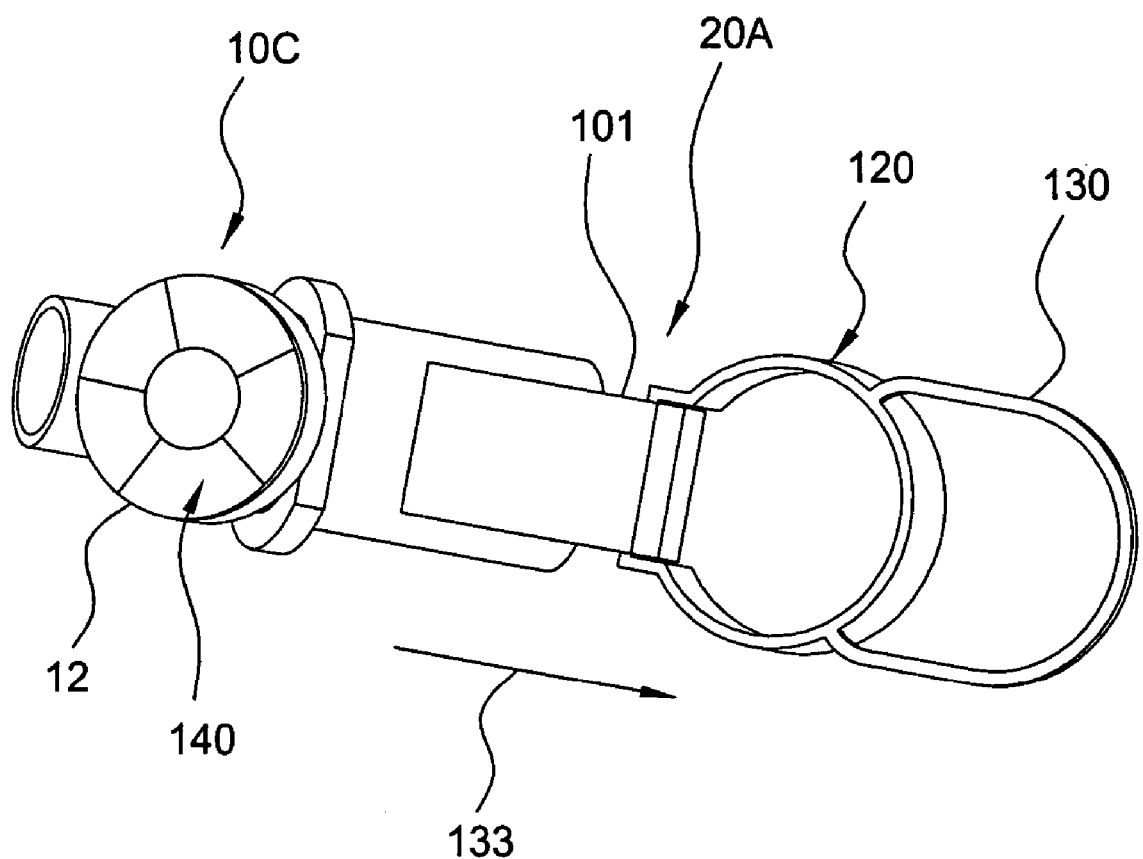
FIG. 33 is an illustration of the removable elongated foldable blocking member from the carbon dioxide indicating apparatus.

It will be further understood from bottom view in FIG. 29 that the inner diameter D4 of the removable cap 120 is suitably dimensioned to permit the cap to engage in a slight interference, or snap fit, over the generally circular disk member 12, FIGS. 1 and 32 comprising the carbon dioxide indicating apparatus 10C. The removable cap 120 is shown in FIG. 26 snap fitted over the generally circular disk member 12 comprising the carbon dioxide indicating apparatus 10C. As will be understood from FIGS. 25-33, the removable end cap 120 may be provided with a loop member 130 for facilitating pulling the cap 120 off of the generally circular disk member 12 (FIG. 32) and pulling the first end 102 of the blocking member 20A out of the carbon dioxide indicating apparatus 10B.

The removable cap 120 may be made, for example, of low density polyethylene and may be made, for example, by injection molding. It will be understood that the thickness of the removable cap top 122, FIGS. 27-31, may be made sufficiently thick that the cap top absorbs, or at least substantially absorbs, ultraviolet radiation and prevents the ultraviolet radiation from reaching the carbon dioxide indicating material 18A, FIG. 21, to initially shield the carbon dioxide indicating material 18A and prevent ultraviolet radiation degradation. In one embodiment, the cap top had a thickness of from 0.045 to 0.055 inches. Alternatively, the removable cap 120 may be made of a suitable color for absorbing, or at least substantially absorbing, ultraviolet radiation, for example, dark blue or black; such colored cap also may be provided with a cap top having the above-noted thickness.

In use, and as illustrated diagrammatically in FIG. 32, the removable cap 120, using the loop member 130, is manually pulled upwardly away from, and unsnapped from, the circular disk 12 comprising the carbon dioxide indicating apparatus 120, as indicated by the curved arrow 132, to expose the carbon dioxide indicating material 18A, FIG. 21, and the carbon dioxide indicating percentage indicia provided on the top surface of the disk 12 to view. Thereafter, as illustrated diagrammatically in FIG. 33, the first end portion 101 of the elongated removable folding member 103, using the loop member 130, is pulled outwardly manually, as indicated by the straight arrow 133 in FIG. 33, to pull the first end portion 101 of the blocking member 20A out of the carbon dioxide indicating apparatus 10C in the same manner described above with respect to the second end portion 101 of the removable blocking member 20A to place the carbon dioxide indicating material 18A, FIG. 21, in fluid communication with the carbon dioxide containing gas 44 and the tubular passageway 15, FIG. 4, and to place the carbon dioxide indicating material 18A in fluid communication with the atmosphere.

Referring again to FIGS. 23, 24, 32 and 33, it will be understood that the top surface of the disk 12 is provided with the same plurality of colored segments and $CO_2$ percentages as shown, for example, in FIG. 1 and described above. In these FIGS., such plurality of colored segments and $CO_2$ percentages are illustrated diagrammatically by the radial or segmental lines indicated by general numerical designation 140.

In brief summary, it will be understood that the further carbon dioxide indicating apparatus embodiments of FIGS. 19-24 and 25-33 permit the carbon dioxide indicating apparatus of the present invention, including the carbon dioxide indicating material subject to ultraviolet degradation, to be preassembled to the above-noted patient respiratory or breathing circuits and in particular to a resuscitator. Such preassesmbly eliminates the loss of valuable life saving time associated with the prior art carbon dioxide indicator containing carbon dioxide indicating material subject to ultraviolet radiation and which must be packaged separately in an ultraviolet shielding package as described above in the BACKGROUND OF THE INVENTION.

It will be understood by those skilled in the art that many modifications and variations may be made in the present invention without departing from the spirit and the scope thereof.

What is claimed is:

1. Carbon dioxide indicating apparatus, comprising:
  a tubular member providing a passageway for having gas containing carbon dioxide flow therethrough;
  a disk member provided transversely at one end of said tubular member, said disk member providing an internal chamber;
  a body of visual indicating material residing in said internal chamber for providing a visible indication upon exposure to the gas containing carbon dioxide; and
  said disk member providing a first opening in fluid communication with said passageway and for placing said indicating material in fluid communication with said passageway to expose said indicating material to the gas containing carbon dioxide and providing a second opening in fluid communication with the atmosphere and for placing said indicating material in fluid communication with the atmosphere, and at least a portion of said disk member being sufficiently transparent to permit said visible indication to be seen therethrough.

2. The apparatus according to claim 1, wherein said disk member includes a base disk provided transversely at one end of said tubular member and a cover disk mounted to and covering said base disk, said base disk and said cover disk including opposed spaced apart central portions providing said internal chamber.

3. The apparatus according to claim 1, wherein said visual indicating material is calorimetric carbon dioxide indicating material which changes color upon exposure to the carbon dioxide to provide the visible indication.

4. The apparatus according to claim 1 wherein said disk member is provided perpendicularly to said one end of said tubular member.

5. The apparatus according to claim 1 wherein said tubular member comprises an elongated hollow tube having an outer diameter and wherein said disk member has an outer diameter larger than the diameter of said tube.

6. The apparatus according to claim 1 wherein said apparatus further comprises removable blocking means operatively associated with said disk member and for initially blocking said first opening and preventing said indicating material from being in fluid communication with said passageway and for initially blocking said second opening and preventing said indicating material from being in fluid communication with the atmosphere and which blocking means upon being removed places said indicating material in fluid communication with said passageway and the atmosphere.

7. The apparatus according to claim 1 wherein said disk member provides said second opening at an angle with respect to said first opening.

8. The apparatus according to claim 7 wherein said disk member provides said second opening disposed substantially perpendicular to said first opening.

9. Carbon dioxide indicating apparatus for indicating the presence of carbon dioxide in gas, comprising:
carbon dioxide indicator including carbon dioxide indicating material for providing a visible indication upon exposure to gas containing carbon dioxide and providing a first opening for communicating the gas to the carbon dioxide indicating material and a second opening for communicating the carbon dioxide indicating material to the atmosphere; and
removable blocking means for initially blocking said first opening and preventing said carbon dioxide indicating material from being in fluid communication with the gas and for initially blocking said second opening and preventing said carbon dioxide indicating material from being in fluid communication with the atmosphere and for initially shielding said carbon dioxide indicating material from ultraviolet radiation.

10. The apparatus according to claim 9, wherein said carbon dioxide indicator includes a base disk provided transversely at one end of said tubular member and a cover disk mounted to and covering said base disk, said base disk and said cover disk including opposed spaced apart central portions providing an internal chamber, said carbon dioxide indicating material residing in said internal chamber.

11. The apparatus according to claim 9 wherein said blocking means comprise a removable elongated foldable blocking member initially covering and blocking said first opening and initially extending through and blocking said second opening and for being folded back upon itself in U-shaped fashion to cover and initially shield said carbon dioxide indicating material from ultraviolet radiation.

12. The apparatus according to claim 9 wherein said blocking means comprise single blocking means.

13. The apparatus according to claim 9 wherein said single blocking means comprise a removable elongated foldable blocking member.

14. The apparatus according to claim 9 wherein said blocking means comprise a removable elongated foldable blocking member including a first end portion overlying and blocking said first opening and extending through and blocking said second opening and including a second end portion folded back over and removably adhered to said carbon dioxide indicator to initially shield said carbon dioxide indicating material from ultraviolet radiation.

15. The apparatus according to claim 14 wherein at least said second end portion of said blocking member includes material for substantially reflecting ultraviolet radiation.

16. The apparatus according to claim 14 wherein said carbon dioxide indicator includes a generally circular disk member, wherein said first end portion of said blocking member is elongated and generally rectangular and wherein said second end portion of said blocking member is an enlarged generally circular second end portion complementary in size and shape to said generally circular disk member.

17. The apparatus according to claim 16 wherein at least said second end portion of said blocking member includes material for substantially reflecting ultraviolet radiation.

18. The indicating apparatus according to claim 9 wherein said removable blocking means comprise a removable cap and a removable elongated foldable blocking member, said cap for being snap fitted over said carbon dioxide indicator to initially shield said carbon dioxide indicating material from ultraviolet radiation, said blocking member including a first end portion secured to said cap and a second end portion for extending through and blocking said second opening and for overlying and blocking said first opening.

19. The apparatus according to claim 18 wherein said cap is a generally cylindrical cap.

20. The apparatus according to claim 18 wherein said cap is made of material for at least substantially absorbing ultraviolet radiation.

21. The apparatus according to claim 20 wherein said cap is provided with a top substantially thick to absorb ultraviolet radiation.

22. The apparatus according to claim 21 wherein said cap top is provided with a dark color for substantially absorbing ultraviolet radiation.

23. The apparatus according to claim 18 wherein said material is a dark material for at least substantially absorbing ultraviolet radiation.

24. The apparatus according to claim 18 wherein said cap is provided with a loop member for facilitating pulling said cap off of said carbon dioxide indicator and for facilitating pulling said blocking member from over said first opening and out of said second opening.

25. The apparatus according to claim 18 wherein said cap includes a generally circular top having a straight rearward portion and which top is circumscribed by a generally perpendicularly downwardly extending wall, said straight portion provided with an opening through which said first end portion of said blocking member extends and which first end portion of said blocking member is secured to said top of said cap.

* * * * *

UNITED STATES PATENT AND TRADEMARK OFFICE
CERTIFICATE OF CORRECTION

| | | |
|---|---|---|
| PATENT NO. | : 7,246,622 B2 | |
| APPLICATION NO. | : 10/926559 | |
| DATED | : July 24, 2007 | |
| INVENTOR(S) | : Geist | |

It is certified that error appears in the above-identified patent and that said Letters Patent is hereby corrected as shown below:

In column 2, line 9, delete "calorimetric" and insert -- colorimetric --, therefor.

In column 2, line 13, delete "calorimetric" and insert -- colorimetric --, therefor.

In column 6, line 28, delete "calorimetric" and insert -- colorimetric --, therefor.

In column 6, lines 30-31, delete "calorimetric" and insert -- colorimetric --, therefor.

In column 6, line 32, delete "calorimetric" and insert -- colorimetric --, therefor.

In column 6, line 36, delete "calorimetric" and insert -- colorimetric --, therefor.

In column 7, line 10, delete "calorimetric" and insert -- colorimetric --, therefor.

In column 7, line 15, delete "calorimetric" and insert -- colorimetric --, therefor.

In column 8, line 27, delete "calorimetric" and insert -- colorimetric --, therefor.

In column 8, line 33, delete "calorimetric" and insert -- colorimetric --, therefor.

In column 9, line 1, delete "calorimetric" and insert -- colorimetric --, therefor.

In column 10, line 5, delete "calorimetric" and insert -- colorimetric --, therefor.

In column 10, line 16, delete "11A." and insert -- 10A. --, therefor.

UNITED STATES PATENT AND TRADEMARK OFFICE
CERTIFICATE OF CORRECTION

PATENT NO. : 7,246,622 B2
APPLICATION NO. : 10/926559
DATED : July 24, 2007
INVENTOR(S) : Geist It is certified that error appears in the above-identified patent and that said Letters Patent is hereby corrected as shown below:

In column 10, line 24, delete "11A." and insert -- 10A. -- , therefor.

In column 11, line 33, delete "11A." and insert -- 10A. --, therefor.

In column 12, line 66, delete "calorimetric" and insert -- colorimetric --, therefor.

In column 13, line 13, delete "calorimetric" and insert -- colorimetric --, therefor.

In column 16, line 26, delete "preassesmbly" and insert -- preassembly --, therefor.

In column 16, line 65, in Claim 3, delete "calorimetric" and insert -- colorimetric --, therefor.

Signed and Sealed this

Twenty-fifth Day of December, 2007

JON W. DUDAS
*Director of the United States Patent and Trademark Office*